(12) United States Patent
Johnson

(10) Patent No.: US 7,956,059 B2
(45) Date of Patent: Jun. 7, 2011

(54) ALIPHATIC AMIDE AND ESTER PYRAZINOYLGUANIDINE SODIUM CHANNEL BLOCKERS

(75) Inventor: Michael R. Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 840 days.

(21) Appl. No.: 11/573,413

(22) PCT Filed: Aug. 18, 2005

(86) PCT No.: PCT/US2005/029275
§ 371 (c)(1), (2), (4) Date: Feb. 8, 2007

(87) PCT Pub. No.: WO2006/023573
PCT Pub. Date: Mar. 2, 2006

(65) Prior Publication Data
US 2009/0227594 A1 Sep. 10, 2009

Related U.S. Application Data

(60) Provisional application No. 60/602,327, filed on Aug. 18, 2004.

(51) Int. Cl.
*A61K 31/4965* (2006.01)
(52) U.S. Cl. .............. 514/255.06; 544/357; 544/386
(58) Field of Classification Search ............ 514/255.06; 544/357, 386
See application file for complete search history.

(56) References Cited

U.S. PATENT DOCUMENTS

| | | |
|---|---|---|
| 6,264,975 B1 | 7/2001 | Boucher, Jr. |
| 6,858,614 B2 | 2/2005 | Johnson |
| 6,858,615 B2 | 2/2005 | Johnson |
| 6,903,105 B2 | 6/2005 | Johnson |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 2004/0198744 A1 | 10/2004 | Johnson |
| 2004/0198747 A1 | 10/2004 | Johnson |
| 2004/0198749 A1 | 10/2004 | Johnson |
| 2004/0204424 A1 | 10/2004 | Johnson |
| 2005/0059676 A1 | 3/2005 | Johnson |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0228182 A1 | 10/2005 | Johnson et al. |
| 2005/0234072 A1 | 10/2005 | Johnson et al. |
| 2006/0040954 A1 | 2/2006 | Johnson |
| 2006/0052394 A1 | 3/2006 | Johnson et al. |
| 2006/0052395 A1 | 3/2006 | Johnson et al. |
| 2006/0063780 A1 | 3/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0032509 A1 | 2/2007 | Johnson et al. |

FOREIGN PATENT DOCUMENTS

| | | |
|---|---|---|
| WO | WO 03/070182 A2 | 8/2003 |
| WO | WO 03/070182 A3 | 8/2003 |
| WO | WO 03/070184 A2 | 8/2003 |
| WO | WO 03/070184 A3 | 8/2003 |
| WO | WO 2004/073629 A2 | 9/2004 |
| WO | WO 2004/073629 A3 | 9/2004 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
Thomas R. Kleyman, et al., "New Amiloride Analogue as Hapten to Raise Anti-Amiloride Antibodies", American Journal of Physiology, vol. 250, pp. C165-0170, 1986.
U.S. Appl. No. 10/920,527, filed Aug. 18, 2004, Hopkins.
U.S. Appl. No. 11/573,693, filed Feb. 14, 2007, Johnson.
U.S. Appl. No. 11/573,421, filed Feb. 8, 2007, Johnson.
U.S. Appl. No. 11/695,936, filed Apr. 3, 2007, Johnson.
U.S. Appl. No. 11/696,003, filed Apr. 3, 2007, Johnson.
U.S. Appl. No. 11/852,003, filed Sep. 7, 2007, Johnson, et al.
U.S. Appl. No. 11/851,803, filed Sep. 7, 2007, Johnson, et al.
U.S. Appl. No. 11/960,989, filed Dec. 20, 2007, Johnson, et al.
U.S. Appl. No. 11/950,674, filed Dec. 5, 2007, Johnson, et al.
U.S. Appl. No. 11/835,902, filed Aug. 8, 2007, Johnson, et al.
U.S. Appl. No. 12/049,946, filed Mar. 17, 2008, Johnson, et al.
U.S. Appl. No. 12/049,968, filed Mar. 17, 2008, Johnson, et al.
U.S. Appl. No. 12/049,894, filed Mar. 17, 2008, Johnson, et al.
U.S. Appl. No. 12/050,010, filed Mar. 17, 2008, Johnson.
U.S. Appl. No. 12/049,993, filed Mar. 17, 2008, Johnson.
U.S. Appl. No. 12/050,019, filed Mar. 17, 2008, Johnson.
U.S. Appl. No. 12/061,837, filed Apr. 3, 2008, Johnson, et al.
U.S. Appl. No. 12/061,864, filed Apr. 3, 2008, Johnson, et al.
U.S. Appl. No. 12/098,581, filed Apr. 7, 2008, Johnson.
U.S. Appl. No. 60/495,725, filed Aug. 18, 2003, Johnson.
U.S. Appl. No. 60/495,720, filed Aug. 18, 2003, Johnson.

(Continued)

*Primary Examiner* — James O Wilson
*Assistant Examiner* — Douglas M Willis
(74) *Attorney, Agent, or Firm* — Oblon, Spivak, McClelland, Maier & Neustadt, L.L.P.

(57) ABSTRACT

The present invention relates to pyrazinoylguanidine compounds represented by formula (I):

where the structural variables are defined herein. The compounds are useful as, for example, sodium channel blockers.

48 Claims, No Drawings

OTHER PUBLICATIONS

U.S. Appl. No. 06/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,814, filed Jul. 11, 2008, Johnson, et al.
U.S. Appl. No. 12/171,867, filed Jul. 11, 2008, Johnson, et al.
U.S. Appl. No. 12/171,897, filed Jul. 11, 2008, Johnson, et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 12/393,252, filed Feb. 26, 2009, Johnson.
U.S. Appl. No. 60/909,802, filed Apr. 3, 2007, Johnson, et al.
U.S. Appl. No. 12/501,654, filed Jul. 13, 2009, Boucher, et al.
U.S. Appl. No. 12/876,615, filed Sep. 7, 2010, Johnson, et al.

* cited by examiner

US 7,956,059 B2

ALIPHATIC AMIDE AND ESTER PYRAZINOYLGUANIDINE SODIUM CHANNEL BLOCKERS

BACKGROUND OF THE INVENTION

1. Field of the Invention

The present invention relates to sodium channel blockers. The present invention also includes a variety of methods of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued Na$^+$ dependent liquid absorption on conjunctional surfaces. In rhinosinusitis, there is an imbalance, as in CB, between mucin secretion and relative ASL depletion. Finally, in the gastrointestinal tract, failure to secrete Cl- (and liquid) in the proximal small intestine, combined with increased Na$^+$ (and liquid) absorption in the terminal ileum leads to the distal intestinal obstruction syndrome (DIOS). In older patients excessive Na$^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMG-CoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds of formula (I) that are more potent and/or absorbed less rapidly and/or exhibit less reversibility, as compared to compounds such as amiloride, benzamil, and phenamil. Therefore, the compounds of formula (I) will give a prolonged pharmacodynamic half-life on mucosal surfaces as compared to known compounds.

It is another aspect of the present invention to provide compounds of formula (I) that are more soluble in aqueous solutions, especially in 0.12-0.9% saline, so that they can be conveniently administered to mucosal surfaces of a patient by suitable means such as a nebulizer, spay, mist or droplets. Therefore, the compounds of formula (I) are more soluble in aqueous solutions as compared to known compounds lacking the additional proanatable nitrogen(s) contained in compounds of Formula (I)

It is another object of the present invention to provide compounds of formula (I) which are (1) absorbed less rapidly from mucosal surfaces, especially airway surfaces, as compared to known compounds and; (2) when absorbed from musosal surfaces after administration to the mucosal surfaces, are converted in vivo into metabolic derivatives thereof which have reduced efficacy in blocking sodium channels as compared to the administered parent compound.

It is another object of the present invention to provide compounds of formula (I) that are more potent and/or absorbed less rapidly and/or exhibit less reversibility, as compared to compounds such as amiloride, benzamil, and phenamil. Therefore, the compounds of formula (I) will give a prolonged pharmacodynamic half-life on mucosal surfaces as compared to previous compounds.

It is another object of the present invention to provide compounds of formula (I) that target the kidney for use in the treatment of cardiovascular disease.

It is another object of the present invention to provide methods of treatment which take advantage of the properties described above.

The objects of the present invention may be accomplished with a class of pyrazinoylguanidine compounds represented by formula (I):

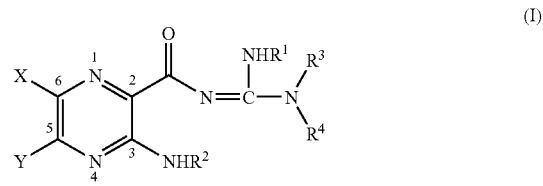

where X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl; Y is hydrogen, hydroxyl, mercapto, lower alkoxy, lower alkyl-thio, halogen, lower alkyl, unsubstituted or substituted mononuclear aryl, or —N(R$^2$)$_2$; R$^1$ is hydrogen or lower alkyl; each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

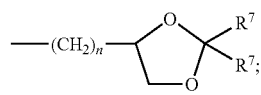

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane; R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

wherein
each R$^L$ is, independently, —R$^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—OR$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

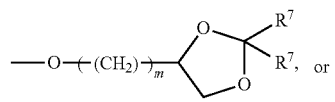

-continued

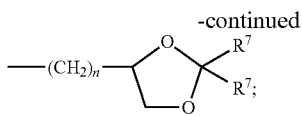

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each o is, independently, an integer from 0 to 10;
each p is an integer from 0 to 10;
with the proviso that the sum of o and p in each contiguous chain is from 1 to 10;
each x is, independently, O, NR$^{10}$, C(=O), CHOH, C(=N—R$^{10}$), CHNR$^7$R$^{10}$, or represents a single bond;
each R$^5$ is independently, —(CH$_2$)$_n$—CO$_2$R$^{13}$, Het-(CH$_2$)$_m$—CO$_2$R$^{13}$, —(CH$_2$)$_n$—Z$_g$—CO$_2$R$^{13}$, Het-(CH$_2$)$_m$—Z$_g$—CO$_2$R$^{13}$, —(CH$_2$)$_n$—NR$^{10}$—(CH$_2$)$_m$(CHOR$^8$)$_n$—CO$_2$R$^{13}$, Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, Het-(CH$_2$)$_m$—(CHOR$^8$)$_m$—CO$_2$R$^{13}$, —(CH$_2$)$_n$—(CHOR$^8$)$_m$—Z$_g$—CO$_2$R$^{13}$, Het-(CH$_2$)$_n$—(CHOR$^8$)$_m$—Z$_g$—CO$_2$R$^{13}$, —(CH$_2$)$_n$—Z$_g$—(CH$_2$)$_m$—CO$_2$R$^{13}$, —(CH$_2$)$_n$—Z$_g$—(CH$_2$)$_m$—CO$_2$R$^{13}$, —(CH$_2$)$_n$—Z$_g$(CHOR$^8$)$_m$—Z$_g$—CO$_2$R$^{13}$, Het-(CH$_2$)$_n$—Z$_g$—(CHOR$^8$)$_m$—Z$_g$—CO$_2$R$^{13}$, —(CH$_2$)$_n$—CONH—C(=NR$^{13}$)—NR$^{13}$R$^{13}$, Het-(CH$_2$)$_n$—CO—NH—C(=NR$^{13}$)—NR$^{13}$R$^{13}$, —(CH$_2$)$_n$—Z$_g$—CONH—C(=NR$^{13}$)—NR$^{13}$R$^{13}$, Het-(CH$_2$)$_n$—Z$_g$—CONH—C(=NR$^{13}$)—NR$^{13}$R$^{13}$, —(CH$_2$)$_n$—NR$^{10}$—(CH$_2$)$_m$(CHOR$^8$)$_n$—CONH—C(=NR$^{13}$)—NR$^{13}$R$^{13}$, Het-(CH$_2$)$_n$—NR$^{10}$—(CH$_2$)$_m$(CHOR$^8$)$_n$—CONH—C(=NR$^{13}$)—NR$^{13}$R$^{13}$, —(CH$_2$)$_n$—(CHOR$^8$)$_m$—CONH—C(=NR$^{13}$)—NR$^{13}$R$^{13}$, Het-(CH$_2$)$_n$—(CHOR$^8$)$_m$—CONH—C(=NR$^{13}$)—NR$^{13}$R$^{13}$, —(CH$_2$)$_n$—(CHOR$^8$)$_m$—Z$_g$—CONH—C(=NR$^{13}$)—NR$^{13}$R$^{13}$, Het-(CH$_2$)$_n$—(CHOR$^8$)$_m$—Z$_g$—CONH—C(=NR$^{13}$)—NR$^{13}$R$^{13}$, —(CH$_2$)$_n$—Z$_g$—(CH$_2$)$_m$CONH—C(=NR$^{13}$)—NR$^{13}$R$^{13}$, —(CH$_2$)$_n$—Z$_g$—(CHOR$^8$)$_m$—Z$_g$—CONH—C(=NR$^{13}$)—NR$^{13}$R$^{13}$, Het-(CH$_2$)$_n$—Z$_g$—(CHOR$^8$)$_m$—Z$_g$—CONH—C(=NR$^{13}$)—NR$^{13}$R$^{13}$, —(CH$_2$)$_n$—CONR$^7$—CONR$^{13}$R$^{13}$, Het-(CH$_2$)$_n$—CONR$^7$—CONR$^{13}$R$^{13}$, —(CH$_2$)$_n$—Z$_g$—CONR$^7$—CONR$^{13}$R$^{13}$, —(CH$_2$)$_n$—Z$_g$—CONR$^7$—CONR$^{13}$R$^{13}$, —(CH$_2$)$_n$—NR$^{10}$—(CH$_2$)$_m$(CHOR$^8$)$_n$—CONR$^7$—CONR$^{13}$R$^{13}$, Het-(CH$_2$)$_n$—NR$^{10}$—(CH$_2$)$_m$(CHOR$^8$)$_n$—CONR$^7$—CONR$^{13}$R$^{13}$, —(CH$_2$)$_n$—(CHOR$^8$)$_m$—CONR$^7$—CONR$^{13}$R$^{13}$, Het-(CH$_2$)$_n$—(CHOR$^8$)$_m$—CONR$^7$—CONR$^{13}$R$^{13}$, —(CH$_2$)$_n$—(CHOR$^8$)$_m$—Z$_g$—CONR$^7$—CONR$^{13}$R$^{13}$, Het-(CH$_2$)$_n$—(CHOR$^8$)$_m$—Z$_g$—CNR$^7$—CONR$^{13}$R$^{13}$, —(CH$_2$)$_n$—Z$_g$—(CH$_2$)$_m$CONR$^7$CONR$^{13}$R$^{13}$, Het-(CH$_2$)$_n$—Z$_g$(CH$_2$)$_m$CONR$^7$—CONR$^{13}$R$^{13}$, —(CH$_2$)$_n$—Z$_g$(CHOR$^8$)$_m$—Z$_g$—CONR$^7$—CONR$^{13}$R$^{13}$, Het-(CH$_2$)$_n$—Z$_g$(CHOR$^8$)$_m$—Z$_g$—CONR$^7$—CONR$^{13}$R$^{13}$, —(CH$_2$)$_n$—CONR$^7$SO$_2$NR$^{13}$R$^{13}$, Het-(CH$_2$)$_m$—CONR$^7$SO$_2$NR$^{13}$R$^{13}$, —(CH$_2$)$_n$—Z$_g$—CONR$^7$SO$_2$NR$^{13}$R$^{13}$, Het-(CH$_2$)$_m$—Z$_g$—CONR$^7$SO$_2$NR$^{13}$R$^{13}$, —(CH$_2$)$_n$—NR$^{10}$—(CH$_2$)$_m$(CHOR$^8$)$_n$—CONR$^7$SO$_2$NR$^{13}$R$^{13}$, Het-(CH$_2$)$_n$—NR$^{10}$—(CH$_2$)$_m$(CHOR$^8$)$_n$—CONR$^7$SO$_2$NR$^{13}$R$^{13}$, —(CH$_2$)$_n$—(CHOR$^8$)$_m$—CONR$^7$SO$_2$NR$^{13}$R$^{13}$, Het-(CH$_2$)$_m$—(CHOR$^8$)$_m$—CONR$^7$SO$_2$NR$^{13}$R$^{13}$, —(CH$_2$)$_n$—(CHOR$^8$)$_m$—Z$_g$—CONR$^7$SO$_2$NR$^{13}$R$^{13}$, Het-(CH$_2$)$_n$—(CHOR$^8$)$_m$—Z$_g$—CONR$^7$SO$_2$NR$^{13}$R$^{13}$, —(CH$_2$)$_n$—Z$_g$—(CH$_2$)$_m$CONR$^7$SO$_2$NR$^{13}$R$^{13}$, Het-(CH$_2$)$_n$—Z$_g$—(CH$_2$)$_m$CONR$^7$SO$_2$NR$^{13}$R$^{13}$, —(CH$_2$)$_n$—Z$_g$—(CHOR$^8$)$_m$—Z$_g$—CONR$^7$SO$_2$NR$^{13}$R$^{13}$, Het-

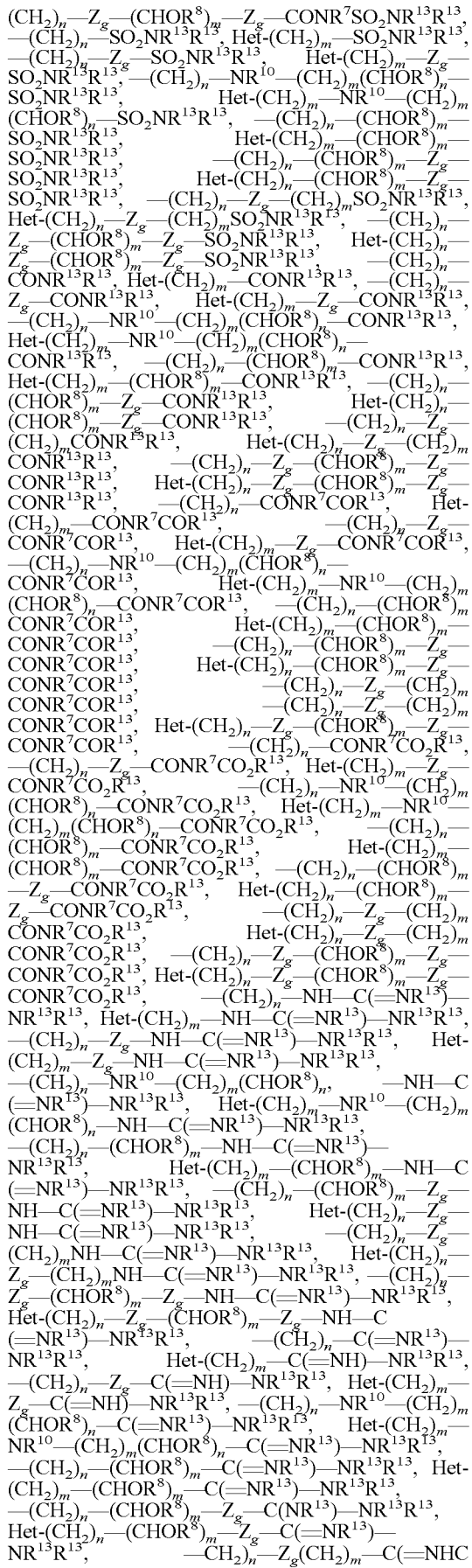

(=NR$^{13}$)—NR$^{13}$R$^{13}$, Het-(CH$_2$)$_n$—Z$_g$—(CH$_2$)$_m$—C (=NR$^{13}$)—NR$^{13}$R$^{13}$, —(CH$_2$)$_n$—Z$_g$—(CHOR$^8$)$_m$— Z$_g$—C(=NR$^{13}$)—NR$^{13}$R$^{13}$, Het-(CH$_2$)$_n$—Z$_g$— (CHOR$^8$)$_m$—Z$_g$—C(=NR$^{13}$)—NR$^{13}$R$^{13}$;

wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, —(CH$_2$)$_n$— NR$^7$R$^{10}$, —O—(CH$_2$)$_m$—NR$^7$R$^{10}$, —(CH$_2$)$_n$(CHOR$^8$) (CHOR$^8$)$_n$—CH$_2$OR$^8$, —O—(CH$_2$)$_m$(CHOR$^8$)(CHOR$^8$)$_n$— CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$ CH$_2$CH$_2$NR$^7$R$^{10}$, —(CH$_2$)$_n$—C(=O)NR$^7$R$^{10}$, —O— (CH$_2$)$_m$—C(=O)NR$^7$R$^{10}$, —(CH$_2$)$_n$—(Z)$_g$—R$^7$, —O— (CH$_2$)$_n$—(Z)$_g$—R$^7$, —(CH$_2$)$_n$—NR$^{10}$—CH$_2$(CHOR$^8$) (CHOR$^8$)$_n$—CH$_2$OR$^8$, —O—(CH$_2$)$_m$—NR$^{10}$—CH$_2$ (CHOR$^8$)(CHOR$^8$)$_n$—CH$_2$OR$^8$, —(CH$_2$)$_n$—CO$_2$R$^7$, —O— (CH$_2$)$_m$—CO$_2$R$^7$, —OSO$_3$H, —O-glucuronide, —O-glucose,

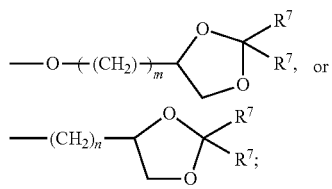

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen lower alkyl, phenyl, substituted phenyl or —CH$_2$(CHOR)$^8$$_m$—R$^{10}$;

each R$^8$ is, independently, hydrogen, lower alkyl, —C(=O)—R$^{11}$, glucuronide, 2-tetrahydropyranyl, or

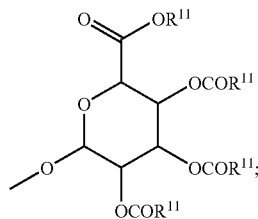

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$, —C(=O)NR$^7$R$^9$, —C(=O)R$^7$, or —(CH$_2$)$_m$—(CHOH)$_n$— CH$_2$OH;

each Z is, independently, CHOH, C(=O), —(CH$_2$)$_n$—, CHNR$^7$R$^{10}$, C=NR$^{10}$, or NR$^{10}$;

each R$^{11}$ is, independently, lower alkyl;

each R$^{12}$ is independently, —SO$_2$CH$_3$, —CO$_2$R$^7$, —C(=O)NR$^7$R$^9$, —C(=O)R$^7$, or —CH$_2$—(CHOH)$_n$— CH$_2$OH;

each R$^{13}$ is, independently, hydrogen, R$^7$, R$^{10}$, —(CH$_2$)$_m$—NR$^7$R$^{10}$, —(CH$_2$)$_m$—NR$^7$R$^7$, —(CH$_2$)$_m$—$\overset{+}{N}$R$^{11}$R$^{11}$R$^{11}$, —(CH$_2$)$_m$—(CHOR$^8$)$_m$—(CH$_2$)$_m$—NR$^7$R$^{10}$, —(CH$_2$)$_m$ —NR$^{10}$R$^{10}$ —(CH$_2$)$_m$—(CHOR$^8$)$_m$—(CH$_2$)$_m$—NR$^7$R$^7$, —(CH$_2$)$_m$—(CHOR$^8$)$_m$—(CH$_2$)$_m$$\overset{+}{N}$R$^{11}$R$^{11}$R$^{11}$,

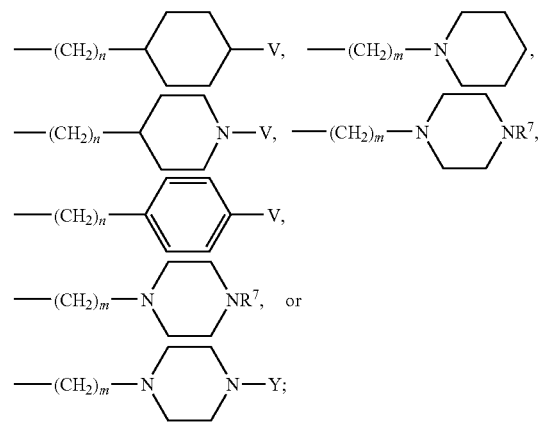

with the proviso that at least one R$^{13}$ must be a group other than hydrogen, R$^7$, or R$^{10}$;

with the further proviso that NR$^{13}$R$^{13}$ can be joined on itself to form a ring comprising one of the following:

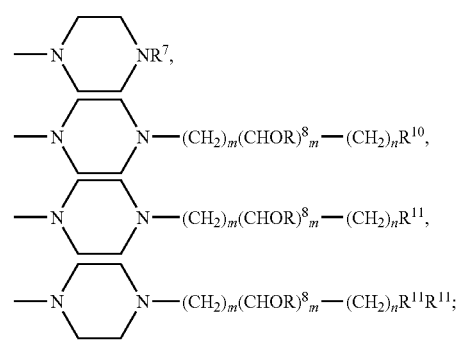

each Het is independently, —NR$^7$, —NR$^{10}$, —S—, —SO—, —SO$_2$—, —O—, —SO$_2$NH—, —NHSO$_2$—, —NR$^7$CO—, or —CONR$^7$—;

each g is, independently, an integer from 1 to 6;
each m is, independently, an integer from 1 to 7;
each n is, independently, an integer from 0 to 7;
each V is, independently, —CH$_2$)$_m$—NR$^7$R$^{10}$, —(CH$_2$)$_m$—NR$^7$R$^7$, —(CH$_2$)$_m$ —(CH$_2$)$_m$—$\overset{+}{N}$R$^{11}$R$^{11}$R$^{11}$, —(CH$_2$)$_n$—(CHOR$^8$)$_m$—(CH$_2$)$_m$NR$^7$R$^{10}$,    —(CH$_2$)$_n$—NR$^{10}$R$^{10}$—CH$_2$)$_n$—(CHOR$^8$)$_m$—(CH$_2$)$_m$NR$^7$R$^7$, —(CH$_2$)$_n$—(CHOR$^8$)$_m$—(CH$_2$)$_m$NR$^{11}$R$^{11}$R$^{11}$,$^+$ with the proviso that when V is attached directly to a nitrogen atom, then V can also be, independently, R$^7$, R$^{10}$, or (R$^{11}$)$_2$;

wherein for any of the above compounds when two —CH$_2$OR$^8$ groups are located 1,2- or 1,3- with respect to each other the R$^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all enantiomers, diastereomers, and racemic mixtures thereof.

In a preferred embodiment, each —(CH$_2$)$_n$—Z$_g$—C(=NH)—NR$^{13}$R$^{13}$ falls within the scope of the structures described above and is, independently, —(CH$_2$)$_n$—CHNH$_2$(C=N)—NR$^{13}$R$^{13}$, In another preferred embodiment, each Het-(CH$_2$)$_m$—NH—C(=NH)—NR$^{13}$R$^{13}$ falls within the scope of the structures described above and is, independently, —(CH$_2$)$_n$—NH—C(=NH)NHR$^{13}$, In another preferred embodiment, each —(CH$_2$)$_n$—Z$_g$—(CHOR$^8$)$_m$—Z$_g$—CONR$^{13}$R$^{13}$ falls within the scope of the structures described above and is, independently, —(CH$_2$)$_n$—CONHCH$_2$(CHOH)$_m$—CONHR$^{13}$, In another preferred embodiment, each Het-(CH$_2$)$_n$—Z$_g$—(CHOR$^8$)$_m$—Z$_g$—CONR$^{13}$R$^{13}$ falls within the scope of the structures described above and is, independently, —NH—C(=O)—CH$_2$—(CHOH)$_n$CH$_2$CONR$^{13}$R$^{13}$ In another a preferred embodiment, each Het-(CH$_2$)$_m$—Z$_g$—C(=NH)—NR$^{13}$R$^{13}$ falls within the scope of the structures described above and is, independently, —O—(CH$_2$)$_m$—NH—C(=NH)—N(R$^{23}$)$_2$, In another a preferred embodiment, each Het-(CH$_2$)$_m$—Z$_g$—CONR$^{13}$R$^{13}$ falls within the scope of the structures described above and is, independently, —O—(CH$_2$)$_m$—CHNH$_2$—CO$_2$NR$^{13}$R$^{13}$ In another preferred embodiment, each R$^5$ falls within the scope of the structures described above and is, independently, —O—CH$_2$CHOHCH$_2$CONR$^{13}$R$^{13}$
—OCH2CHOHCH$_2$CO$_2$R$^{13}$OCH$_2$CH$_2$CONR$^{13}$R$^{13}$
—OCH$_2$CH$_2$NHCOR$^{13}$
—CH$_2$CH$_2$CONR$^{13}$R$^{13}$
—OCH$_2$CH$_2$CONR$^{13}$R$^{13}$O—(CH$_2$)$_m$—CO$_2$R$^{13}$
—(CH$_2$)$_m$—CO$_2$R$^{13}$
—OCH$_2$CH$_2$CO$_2$R$^{13}$
—OCH$_2$CO$_2$R$^{13}$
—O—(CH$_2$)$_m$—NH—C(=NH)—NR$^{13}$)$_2$,
—(CH$_2$)$_n$—NH—C(=NH)—N(R$^{13}$)$_2$,
—NHCH$_2$(CHOH)$_2$—CCONR$^{13}$R$^{13}$
—OCH$_2$CO$_2$R$^{13}$
—NHSO$_2$(CH2)$_2$CONR$^{13}$R$^{13}$
—(CH$_2$)$_m$—NH—C(=O)—OR$^{13}$
—O—(CH$_2$)$_m$—NH—C(=O)—OR$^{13}$,
—(CH$_2$)$_n$—NH—C(=O)—R$^{13}$,
—O—(CH$_2$)$_m$—NH—C(=O)—R$^{13}$,
—O—CH$_2$C(=ONR$^{13}$R$^{13}$
—CH$_2$NCO$_2$R$^{13}$
—NHCO$_2$R$^{13}$
—OCH$_2$CH$_2$CH$_2$CH$_2$CONR$^{13}$R$^{13}$
—SO$_2$CH$_2$CH$_2$CONR$^{13}$R$^{13}$
—OCH$_2$CH$_2$CHOHCH$_2$CONR$^{13}$R$^{13}$
—OCH$_2$CH$_2$NHCO$_2$R$^{13}$
—NH—C(=NH2)-NR$^{13}$R$^{13}$
—OCH$_2$-(α—CHOH)$_2$—CONR$^{13}$R$^{13}$
—OCH$_2$CHOHCH$_2$CONHR$^{13}$
—(CH$_2$)$_m$—CHOH—CH$_2$—NHCO$_2$R$^{13}$
—O—(CH$_2$)$_m$—CHOH—CH$_2$—CO$_2$R$^{13}$
—(CH$_2$)$_m$—NHC(O)OR$^{13}$
—O—(CH$_2$)$_m$—NHC(O)OR$^{13}$
—OCH$_2$CH$_2$CONHR$^{13}$
—OCH$_2$CH$_2$NHCH$_2$(CHOH)$_2$CH$_2$CONHR$^{13}$
—OCH$_2$CH$_2$CONH(CH$_2$[(CHOH)$_2$CH$_2$NH$_2$)]$_2$,
—(CH$_2$)$_4$—NHCO$_2$R$^{13}$,
—(CH$_2$)$_4$—CONR$^{13}$R$^{13}$,
—(CH$_2$)$_4$—CO$_2$R$^{13}$
—OCH$_2$CH$_2$CONHSOCH$_2$CH$_2$N(CH$_3$)$_2$
—O—(CH$_2$)$_m$—C(=NH)—N(R$^{13}$)$_2$,
—(CH$_2$)$_n$—C(=NH)—N(R$^{13}$)$_2$,
—(CH$_2$)$_3$—NHCO$_2$R$^{13}$—(CH$_2$)$_3$CONHCO$_2$R$^{13}$
—O—(CH$_2$)$_m$—NH—NH—C(=NH)—N(R$^{13}$)$_2$,
—(CH$_2$)$_n$—NH—NH—C(=NH)—N(R$^{13}$)$_2$, or
—O—CH$_2$—CHOH—CH$_2$—NH—C(=NH)—N(R$^{13}$)$_2$;

In another preferred embodiment of the present invention the compound of formula (1) is represented by the formula:

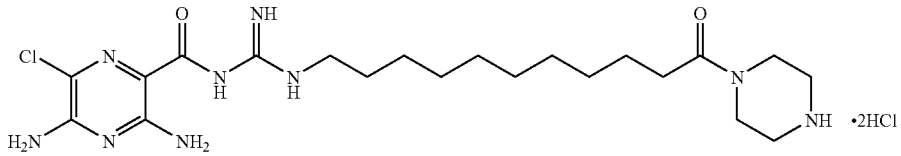

In another preferred embodiment of the present invention the compound of formula (1) is represented by the formula:

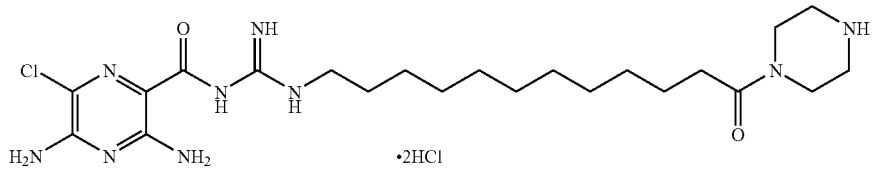

In another preferred embodiment of the present invention the compound of formula (1) is represented by the formula:

[Chemical structure: 3,5-diamino-6-chloropyrazine-2-carboxamide linked through acylguanidine to a decyl chain, terminating in an amide with 3-(dimethylamino)propyl group; ·2HCl salt]

In another preferred embodiment of the present invention the compound of formula (1) is represented by the formula:

[Chemical structure: same as above without the ·2HCl notation, shown with NMe₂ terminus]

The present also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC, comprising:
contacting sodium channels with an effective amount of a compound represented by formula (I).

The present invention also provides a method of promoting mucus clearance in mucosal surfaces, comprising:
administering an effective amount of a compound represented by formula (I) to a mucosal surface of a subject.

The present invention also provides a method of treating chronic bronchitis, comprising:
administering an effective amount of a compound represented by formula (I) to a subject in need thereof.

The present invention also provides a method of treating cystic fibrosis, comprising:
administering an effective amount of compound represented by formula (I) to a subject in need thereof.

The present invention also provides a method of treating rhinosinusitis, comprising:
administering an effective amount of a compound represented by a formula (I) to a subject in need thereof.

The present invention also provides a method of treating nasal dehydration, comprising:
administering an effective amount of a compound represented by formula (I) to the nasal passages of a subject in need thereof.

In a specific embodiment, the nasal dehydration is brought on by administering dry oxygen to the subject.

The present invention also provides a method of treating sinusitis, comprising:
administering an effective amount of a compound represented by formula (I) to a subject in need thereof.

The present invention also provides a method of treating pneumonia, comprising:
administering an effective amount of a compound represented by formula (I) to a subject in need thereof.

The present invention also provides a method of preventing ventilator-induced pneumonia, comprising:
administering an effective compound represented by formula (I) to a subject by means of a ventilator.

The present invention also provides a method of treating asthma, comprising:
administering an effective amount of a compound represented by formula (I) to a subject in need thereof.

The present invention also provides a method of treating primary ciliary dyskinesia, comprising:
administering an effective amount of a compound represented by formula (I) to a subject in need thereof.

The present invention also provides a method of treating otitis media, comprising:
administering an effective amount of a compound represented by formula (I) to a subject in need thereof.

The present invention also provides a method of inducing sputum for diagnostic purposes, comprising:
administering an effective amount of compound represented by formula (I) to a subject in need thereof.

The present invention also provides a method of treating chronic obstructive pulmonary disease, comprising:
administering an effective amount of a compound represented by formula (I) to a subject in need thereof.

The present invention also provides a method of treating emphysema, comprising:
administering an effective amount of a compound represented by formula (I) to a subject in need thereof.

The present invention also provides a method of treating dry eye, comprising:
administering an effective amount of a compound represented by formula (I) to the eye of the subject in need thereof.

The present invention also provides a method of promoting ocular hydration, comprising:
administering an effective amount of a compound represented by formula (I) to the eye of the subject.

The present invention also provides a method of promoting corneal hydration, comprising:
  administering an effective amount of a compound represented by formula (I) to the eye of the subject.

The present invention also provides a method of treating Sjögren's disease, comprising:
  administering an effective amount of compound represented by formula (I) to a subject in need thereof.

The present invention also provides a method of treating vaginal dryness, comprising:
  administering an effective amount of a compound represented by formula (I) to the vaginal tract of a subject in need thereof.

The present invention also provides a method of treating dry skin, comprising:
  administering an effective amount of a compound represented by formula (I) to the skin of a subject in need thereof.

The present invention also provides a method of treating dry mouth (xerostomia), comprising:
  administering an effective amount of compound represented by formula (I) to the mouth of the subject in need thereof.

The present invention also provides a method of treating distal intestinal obstruction syndrome, comprising:
  administering an effective amount of compound represented by formula (I) to a subject in need thereof.

The present invention also provides a method of treating esophagitis, comprising:
  administering an effective amount of a compound represented by formula (I) to a subject in need thereof.

The present invention also provides a method of treating constipation, comprising:
  administering an effective amount of a compound represented by formula (I) to a subject in need thereof. In one embodiment of this method, the compound is administered either orally or via a suppository or enema.

The present invention also provides a method of treating chronic diverticulitis comprising:
  administering an effective amount of a compound represented by formula (I) to a subject in need thereof.

The present invention also provides a method of treating hypertension, comprising administering the compound represented by formula (I) to a subject in need thereof.

The present invention also provides a method of reducing blood pressure, comprising administering the compound represented by formula (I) to a subject in need thereof.

The present invention also provides a method of treating edema, comprising administering the compound represented by formula (I) to a subject in need thereof.

The present invention also provides a method of promoting diuresis, comprising administering the compound represented by formula (I) to a subject in need thereof.

The present invention also provides a method of promoting natriuresis, comprising administering the compound represented by formula (I) to a subject in need thereof.

The present invention also provides a method of promoting saluresis, comprising administering the compound represented by formula (I) to a subject in need thereof.

DETAILED DESCRIPTION OF THE INVENTION

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (I) are more soluble in aqueous solutions, especially in 0.12-0.9% saline, so that they can be conveniently administered to mucosal surfaces of a patient by suitable means such as a nebulizer, spay, mist or droplets. Therefore, the compounds of formula (I) are more soluble in aqueous solutions as compared to known compounds lacking an additional proatonateable nitrogen In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cyloalkyl, mononuclear aryl, or —N(R$^2$)$_2$. The alkyl moiety of the lower alkoxy groups is the same as described above. Examples of mononuclear aryl include phenyl groups. The phenyl group may be unsubstituted or substituted as described above. The preferred identity of Y is —N(R$^2$)$_2$. Particularly preferred are such compounds where each R$^2$ is hydrogen.

R$^1$ may be hydrogen or lower alkyl. Hydrogen is preferred for R$^1$.

Each R$^2$ may be, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_n$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

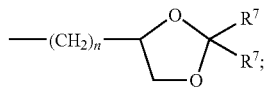

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety —$(C(R^L)_2)_o$-x—$(C(R^L)_2)_p$— defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, C(=O), CHOH, C(=N—$R^{10}$), $CHNR^7R^{10}$, or represents a single bond;

Therefore, when x represents a single bond, the alkylene chain bonded to the ring is represented by the formula —$(C(R^L)_2)_{o+p}$—, in which the sum o+p is from 1 to 10.

Each $R^L$ may be, independently, —$R^7$, —$(CH_2)_n$—$OR^8$, —O—$(CH_2)_n$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

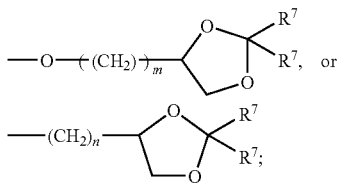

or

The preferred $R^L$ groups include —H, —OH, —$N(R^7)_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —$CHR^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula —$(CH_2)_o$—x—$(CH_2)_p$—.

There is one $R^5$ present in formula (A). Each $R^5$ may be, independently,

—$(CH_2)_n$—$CO_2R^{13}$, Het-$(CH_2)_m$—$CO_2R^{13}$, —$(CH_2)_n$—$Z_g$—$CO_2R^{13}$, Het-$(CH_2)_m$—$Z_g$—$CO_2R^{13}$, —$(CH_2)_n$—$NR^{10}$—$(CH_2)_m(CHOR^8)_n$—$CO_2R^{13}$, Het-$(CH_2)_m$—$NR^{10}$—$(CH_2)_m(CHOR^8)_n$—$CO_2R^{13}$, —$(CH_2)_n$—$(CHOR^8)_m$—$CO_2R^{13}$, Het-$(CH_2)_m$—$(CHOR^8)_m$—$CO_2R^{13}$, —$(CH_2)_n$—$(CHOR^8)_m$—$Z_g$—$CO_2R^{13}$, Het-$(CH_2)_n$—$(CHOR^8)_m$—$Z_g$—$CO_2R^{13}$, —$(CH_2)_m$—$Z_g$—$(CH_2)_m$—$CO_2R^{13}$, —$(CH_2)_m$—$CO_2R^{13}$, —$(CH_2)_n$—$Z_g$—$(CH_2)_m$—$CO_2R^{13}$, —$(CH_2)_n$—$Z_g$—$(CHOR^8)_m$—$Z_g$—$CO_2R^{13}$, Het-$(CH_2)_n$—$Z_g$—$(CHOR^8)_m$—$Z_g$—$CO_2R^{13}$, —$(CH_2)_n$—CONH—C(=$NR^{13}$)—$NR^{13}R^{13}$, Het-$(CH_2)_n$—CO—NH—C(=$NR^{13}$)—$NR^{13}R^{13}$, —$(CH_2)_n$—CONH—C(=$NR^{13}$)—$NR^{13}R^{13}$, Het-$(CH_2)_n$—$Z_g$—CONH—C(=$NR^{13}$)—$NR^{13}R^{13}$, —$(CH_2)_n$—$NR^{10}$—$(CH_2)_m(CHOR^8)_n$—CONH—C(=$NR^{13}$)—$NR^{13}R^{13}$, Het-$(CH_2)_n$—$NR^{10}$—$(CH_2)_m(CHOR^8)_n$—CONH—C(=$NR^{13}$)—$NR^{13}R^{13}$, —$(CH_2)_n$—$(CHOR^8)_m$—CONH—C(=$NR^{13}$)—$NR^{13}R^{13}$, Het-$(CH_2)_n$—$(CHOR^8)_m$—CONH—C(=$NR^{13}$)—$NR^{13}R^{13}$, —$(CH_2)_n$—$(CHOR^8)_m$—$Z_g$—CONH—C(=$NR^{13}$)$NR^{13}R^{13}$, Het-$(CH_2)_n$—$(CHOR^8)_m$—$Z_g$—CONH—C(=$NR^{13}$)—$NR^{13}R^{13}$, —$(CH_2)_n$—$Z_g$—$(CH_2)_m$—CONH—C(=$NR^{13}$)—$NR^{13}R^{13}$, Het-$(CH_2)_n$—$Z_g$—$(CH_2)_m$CONH—C(=$NR^{13}$)_$NR^{13}R^{13}$, —$(CH_2)_n$—$Z_g$—$(CHOR^8)_m$—$Z_g$—CONH—C(=$NR^{13}$)—$NR^{13}R^{13}$, Het-$(CH_2)_n$—$Z_g$—$(CHOR^8)_m$—$Z_g$—CONH—C(=$NR^{13}$)$NR^{13}R^{13}$—$(CH_2)_n$—$CONR^7$—$CONR^{13}R^{13}$, Het-$(CH_2)_n$—$CONR^7$—$CONR^{13}R^{13}$, —$(CH_2)_n$—$Z_g$—$CONR^7$—$CONR^{13}R^{13}$, —$(CH_2)_n$—$Z_g$—$CONR^7$—$CONR^{13}R^{13}$, —$(CH_2)_n$—$NR^{10}$—$(CH_2)_m(CHOR^8)_n$—$CONR^7$—$CONR^{13}R^{13}$, Het-$(CH_2)_n$—$NR^{10}$—$(CH_2)_m(CHOR^8)_n$—$CONR^7$—$CONR^{13}R^{13}$, —$(CH_2)_n$—$(CHOR^8)_m$—$CONR^7$—$CONR^{13}R^{13}$, Het-$(CH_2)_n$—$(CHOR^8)_m$—$CONR^7$—$CONR^{13}R^{13}$, —$(CH_2)_n$—$(CHOR^8)_n$—$Z_g$—$CONR^7CONR^{13}R^{13}$, Het-$(CH_2)_n$—$(CHOR^8)_m$—$Z_g$—$CNR^7$—$CONR^{13}R^{13}$, —$(CH_2)_n$—$Z_g$—$(CH_2)_m$—$CONR^7$—$CONR^{13}R^{13}$, Het-$(CH_2)_n$—$Z_g$—$(CH_2)_m$—$CONR^7$—$CONR^{13}R^{13}$, —$(CH_2)_n$—$Z_g$—$(CHOR^8)_m$—$Z_g$—$CONR^7$—$CONR^{13}R^{13}$, Het-$(CH_2)_n$—$Z_g$—$(CHOR^8)_n$—$Z_g$—$CONR^7$—$CONR^{13}R^{13}$, —$(CH_2)_n$—$CONR^7SO_2NR^{13}R^{13}$, Het-$(CH_2)_m$—$CONR^7SO_2NR^{13}R^{13}$, —$(CH_2)_n$—$Z_g$—$CONR^7SO_2NR^{13}R^{13}$, Het-$(CH_2)_m$—$Z_g$—$CONR^7SO_2NR^{13}R^{13}$, —$(CH_2)_n$—$NR^{10}$—$(CH_2)_m$—$(CHOR^8)_n$—$CONR^7SO_2NR^{13}R^{13}$, Het-$(CH_2)_m$—$NR^{10}$—$(CH_2)_m(CHOR^8)_n$—$CONR^7SO_2NR^{13}R^{13}$, —$(CH_2)_n$—$(CHOR^8)_m$$CONR^7SO_2NR^{13}R^{13}$, Het-$(CH_2)_m$—$(CHOR^8)_m$—$CONR^7SO_2NR^{13}R^{13}$, —$(CH_2)_n$—$(CHOR^8)_m$—$Z_g$—$CONR^7SO_2NR^{13}R^{13}$, Het-$(CH_2)_n$—$(CHOR^8)_m$—$Z_g$—$CONR^7SO_2NR^{13}R^{13}$, —$(CH_2)_n$—$Z_g$—$(CH_2)_m CONR^7SO_2NR^{13}R^{13}$, Het-$(CH_2)_n$—$Z_g$—$(CH_2)_m CONR^7SO_2NR^{13}R^{13}$, —$(CH_2)_n$—$Z_g$—$(CHOR^8)_m$—$Z_g$—$CONR^7SO_2NR^{13}R^{13}$, Het-$(CH_2)_n$—$Z_g$—$(CHOR^8)_m$—$Z_g$—$CONR^7SO_2NR^{13}R^{13}$—$(CH_2)_m$—$SO_2NR^{13}R^{13}$, Het-$(CH_2)_m$—$SO_2NR^{13}R^{13}$, —$(CH_2)_n$—$Z_g$—$SO_2NR^{13}R^{13}$, Het-$(CH_2)_m$—$Z_g$—$SO_2NR^{13}R^{13}$, —$(CH_2)_n$—$NR^{10}$—$(CH_2)_m(CHOR^8)_n$—$SO_2NR^{13}R^{13}$, Het-$(CH_2)_m$—$NR^{10}$—$(CH_2)_m(CHOR^8)_n$—$SO_2NR^{13}R^{13}$, —$(CH_2)_n$—$(CHOR^8)_m$—$SO_2NR^{13}R^{13}$, Het-$(CH_2)_m$—$(CHOR^8)_m SO_2NR^{13}R^{13}$, —$(CH_2)_n$—$(CHOR^8)_m$—$Z_g$—$SO_2NR^{13}R^{13}$, Het-$(CH_2)_n$—$(CHOR^8)_m$—$Z_g$—$SO_2NR^{13}R^{13}$, —$(CH_2)_n$—$Z_g$—$(CH_2)_m SO_2NR^{13}R^{13}$, Het-$(CH_2)_n$—$Z_g$—$(CH_2)_m SO_2NR^{13}R^{13}$, —$(CH_2)_n$—$Z_g$—$(CHOR^8)_m$—$Z_g$—

$SO_2NR^{13}R^{13}$, Het-$(CH_2)_n$—$Z_g$—$(CHOR^8)_m$—$Z_g$—$SO_2NR^{13}R^{13}$, —$(CH_2)_n$—$CONR^{13}R^{13}$, Het-$(CH_2)_m$—$CONR^{13}R^{13}$, —$(CH_2)_n$—$Z_g$—$CONR^{13}R^{13}$, Het-$(CH_2)_m$—$Z_g$—$CONR^{13}R^{13}$, —$(CH_2)_n$—$NR^{10}$—$(CH_2)_m(CHOR^8)_n$—$CONR^{13}R^{13}$, Het-$(CH_2)_m$—$NR^{10}$—$(CH_2)_m(CHOR^8)_n$—$CONR^{13}R^{13}$, —$(CH_2)_n$—$(CHOR^8)_m$—$CONR^{13}R^{13}$, Het-$(CH_2)_m$—$(CHOR^8)_m$—$CONR^{13}R^{13}$, —$(CH_2)_n$—$(CHOR^8)_m$—$Z_g$—$CONR^{13}R^{13}$, Het-$(CH_2)_n$—$(CHOR^8)_m$—$Z_g$—$CONR^{13}R^{13}$, —$(CH_2)_n$—$Z_g$—$(CH_2)_mCONR^{13}R^{13}$, Het-$(CH_2)_n$—$Z_g$—$(CH_2)_mCONR^{13}R^{13}$, —$(CH_2)_n$—$Z_g$—$(CHOR^8)_m$—$Z_g$—$CONR^{13}R^{13}$, Het-$(CH_2)_n$—$Z_g$—$(CHOR^8)_m$—$Z_g$—$CONR^{13}R^{13}$, —$(CH_2)_n$—$CONR^7COR^{13}$, Het-$(CH_2)_m$—$CONR^7COR^{13}$, —$(CH_2)_n$—$Z_g$—$CONR^7COR^{13}$, Het-$(CH_2)_m$—$Z_g$—$CONR^7COR^{13}$, —$(CH_2)_n$—$NR^{10}$—$(CH_2)_m(CHOR^8)_n$—$CONR^7COR^{13}$, Het-$(CH_2)_m$—$NR^{10}$—$(CH_2)_m(CHOR^8)_n$—$CONR^7COR^{13}$, —$(CH_2)_n$—$(CHOR^8)_m$—$CONR^7COR^{13}$, Het-$(CH_2)_m$—$(CHOR^8)_g$—$CONR^7COR^{13}$—$(CH_2)_n(CHOR^8)_m$—$Z_g$—$CONR^7COR^{13}$, Het-$(CH_2)_n$—$(CHOR^8)_m$—$Z_g$—$CONR^7COR^{13}$, —$(CH_2)_n$—$Z_g$—$(CH_2)_mCONR^7COR^{13}$, —$(CH_2)_n$—$Z_g$—$(CH_2)_mCONR^7COR^{13}$, Het-$(CH_2)_n$—$Z_g$—$(CHOR^8)_m$—$Z_g$—$CONR^7COR^{13}$, —$(CH_2)_n$—$CONR^7CO_2R^{13}$, —$(CH_2)_n$—$Z_g$—$CONR^7CO_2R^{13}$, Het-$(CH_2)_m$—$Z_g$—$CONR^7CO_2R^{13}$, —$(CH_2)_n$—$NR^{10}$—$(CH_2)_m(CHOR^8)_n$—$CONR^7CO_2R^{13}$, Het-$(CH_2)_m$—$NR^{10}$—$(CH_2)_m(CHOR^8)_n$—$CONR^7CO_2R^{13}$, —$(CH_2)_n$—$(CHOR^8)_m$—$CONR^7CO_2R^{13}$, Het-$(CH_2)_m$—$(CHOR^8)_n$—$CONR^7CO_2R^{13}$, —$(CH_2)_n$—$(CHOR^8)_m$—$Z_g$—$CONR^7CO_2R^{13}$, Het-$(CH_2)_n$—$(CHOR^8)_m$—$Z_g$—$CONR^7CO_2R^{13}$, —$(CH_2)_n$—$Z_g$—$(CH_2)_mCONR^7CO_2R^{13}$, Het-$(CH_2)_n$—$Z_g$—$(CH_2)_mCONR^7CO_2R^{13}$—$(CH_2)_n$—$Z_g$—$(CHOR^8)_m$—$Z_g$—$CONR^7CO_2R^{13}$, Het-$(CH_2)_n$—$Z_g$—$(CHOR^8)_m$—$Z_g$—$CONR^7CO_2R^{13}$, —$(CH_2)_n$—$NH$—$C(=NR^{13})$—$NR^{13}R^{13}$, Het-$(CH_2)_m$—$NH$—$C(=NR^{13})$—$NR^{13}R^{13}$, —$(CH_2)_n$—$Z_g$—$NH$—$C(=NR^{13})$—$NR^{13}R^{13}$, Het-$(CH_2)_m$—$Z_g$—$NH$—$C(=NR^{13})$—$NR^{13}R^{13}$, —$(CH_2)_n$—$NR^{10}$—$(CH_2)_m(CHOR^8)_n$—$NH$—$C(=NR^{13})$—$NR^{13}R^{13}$, Het-$(CH_2)_m$—$NR^{10}$—$(CH_2)_m(CHOR^8)_n$—$NH$—$C(=NR^{13})$—$NR^{13}R^{13}$, —$(CH_2)_n$—$(CHOR^8)_m$—$NH$—$C(=NR^{13})$—$NR^{13}R^{13}$, Het-$(CH_2)_m$—$(CHOR^8)_m$—$NH$—$C(=NR^{13})$—$NR^{13}R^{13}$, —$(CH_2)_n$—$(CHOR^8)_m$—$Z_g$—$NH$—$C(=NR^{13})$—$NR^{13}R^{13}$, Het-$(CH_2)_n$—$(CHOR^8)_m$—$Z_g$—$NH$—$C(=NR^{13})$—$NR^{13}R^{13}$, —$(CH_2)_n$—$Z_g$—$(CH_2)_mNH$—$C(=NR^{13})$—$NR^{13}R^{13}$, Het-$(CH_2)_n$—$Z_g$—$(CH_2)_mNH$—$C(=NR^{13})$—$NR^{13}R^{13}$, —$(CH_2)_n$—$Z_g$—$(CHOR^8)_m$—$Z_g$—$NH$—$C(=NR^{13})$—$NR^{13}R^{13}$, Het-$(CH_2)_n$—$Z_g$—$(CHOR^8)_m$—$Z_g$—$NH$—$C(=NR^{13})$—$NR^{13}R^{13}$, —$(CH_2)_n$—$C(=NR^{13})$—$NR^{13}R^{13}$, Het-$(CH_2)_m$—$C(=NH)$—$NR^{13}R^{13}$, —$(CH_2)_n$—$Z_g$—$C(=NH)$$NR^{13}R^{13}$, Het-$(CH_2)_m$—$Z_g$—$C(=NH)$—$NR^{13}R^{13}$—$(CH_2)_n$—$NR^{10}$—$(CH_2)_m(CHOR^8)_n$—$C(=NR^{13})$—$NR^{13}R^{13}$, Het-$(CH_2)_m$—$NR^{10}$—$(CH_2)_m(CHOR^8)_n$—$C(=NR^{13})$—$NR^{13}R^{13}$, —$(CH_2)_n$—$(CHOR^8)_m$—$C(=NR^{13})$—$NR^{13}R^{13}$, Het-$(CH_2)_m$—$(CHOR^8)_m$—$C(=NR^{13})$—$NR^{13}R^{13}$, —$(CH_2)_n$—$(CHOR^8)_m$—$Z_g$—$C(=NR^{13})$—$NR^{13}R^{13}$, Het-$(CH_2)_n(CHOR^8)_m$—$Z_g$—$C(=NR^{13})$—$NR^{13}R^{13}$, —$(CH_2)_n$—$Z_g$—$(CH_2)_m$—$C(=NHC(=NR^{13})$—$NR^{13}R^{13}$, Het-$(CH_2)_n$—$Z_g$—$(CH_2)_m$—$C(=NR^{13})$—$NR^{13}R^{13}$, —$(CH_2)_n$—$Z_g$—$(CHOR^8)_n$—$Z_g$—$C(=NR^{13})$—$NR^{13}R^{13}$, Het-$(CH_2)_n$—$Z_g$—$(CHOR^8)_m$—$Z_g$—$C(=NR^{13})$—$NR^{13}R^{13}$;

with the proviso wherein when two —$CH_2OR^8$ groups are located 1,2- or 1,3- with respect to each other the $R^8$ groups may be joined to form a cyclic mono- or di-substituted 1,3-dioxane or 1,3-dioxolane;

In a preferred embodiment, each —$(CH_2)_n$—$Z_g$—$C(=NH)$—$NR^{13}R^{13}$ falls within the scope of the structures described above and is, independently, —$(CH_2)_n$—$CHNH(C=N)$—$NR^{13}R^{13}$, In another preferred embodiment, each, Het-$(CH_2)_m$—$NH$—$C(=NH)$—$NR^{13}R^{13}$ falls within the scope of the structures described above and is, independently, —$(CH_2)_n$—$NH$—$C(=NH)NHR^{13}$, In another preferred embodiment, each —$(CH_2)_n$—$Z_g$—$(CHOR^8)_m$—$Z_g$—$CONR^{13}R^{13}$ falls within the scope of the structures described above and is, independently, —$(CH_2)_n$—$CONHCH_2(CHOH)_m$—$CONHR^{13}$, In another preferred embodiment, each Het-$(CH_2)_n$—$Z_g$—$(CHOR^8)_n$—$Z_g$—$CONR^{13}R^{13}$ falls within the scope of the structures described above and is, independently, —$NH$—$C(=O)$—$CH_2$—$(CHOH)_nCH_2CONR^{13}R^{13}$ In another a preferred embodiment, each Het-$(CH_2)_m$—$Z_g$—$C(=NH)$—$NR^{13}R^{13}$ falls within the scope of the structures described above and is, independently, —$O$—$(CH_2)_m$—$NH$—$C(=NH)$—$N(R^{13})_2$, In another a preferred embodiment, each Het-$(CH_2)_m$—$Z_g$—$CONR^{13}R^{13}$ falls within the scope of the structures described above and is, independently, —$O$—$(CH_2)_m$—$CHNH_2CO_2NR^{13}R^{13}$ In another preferred embodiment, each $R^5$ falls within the scope of the structures described above and is, independently,
—$O$—$CH_2CHOHCH_2CONR^{13}R^{13}$
—$OCH2CHOHCH_2CO_2R^{13}OCH_2CH_2CONR^{13}R^{13}$
—$OCH_2CH_2NHCOR^{13}$
—$CH_2CH_2CONR^{13}R^{13}$
—$OCH_2CH_2CONR^{13}R^{13}O$—$(CH_2)_m$—$CO_2R^{13}$
—$(CH_2)_m$—$CO_2R^{13}$
—$OCH_2CH_2CO_2R^{13}$
—$OCH_2CO_2R^{13}$
—$O$—$(CH_2)_m$—$NH$—$C(=NH)$—$NR^{13})_2$,
—$(CH_2)_m$—$NH$—$C(=NH)$—$N(R^{13})_2$,
—$NHCH_2(CHOH)_2$—$CONR^{13}R^{13}$
—$OCH_2CO_2R^{13}$
—$NHSO_2(CH_2)_2CONR^{13}R^{13}$
—$(CH_2)_m$—$NH$—$C(=O)$—$OR^{13}$
—$O$—$(CH_2)_m$—$NH$—$C(=O)\_OR^{13}$,
—$(CH_2)_m$—$NH$—$C(=O)$—$R^{13}$,
—$O$—$(CH_2)_m$—$NH$—$C(=O)$—$R^{13}$
—$O$—$CH_2C(=ONR^{13}R^{13}$
—$CH_2NCO_2R^{13}$
—$NHCO_2R^{13}$
—$OCH_2CH_2CH_2CH_2CONR^{13}R^{13}$
—$SO_2CH_2CH_2CONR^{13}R^{13}$
—$OCH_2CH_2CHOHCH_2CONR^{13}R^{13}$
—$OCH_2CH_2NHCO_2R^{13}$
—$NH$—$C(=NH2)$-$NR^{13}R^{13}$
—$OCH_2(\alpha$—$CHOH)_2$—$CONR^{13}R^{13}$
—$OCH_2CHOHCH_2CONHR^{13}$
—$(CH_2)_m$—$CHOH$—$CH_2$—$NHCO_2R^{13}$
—$O$—$(CH_2)_m$—$CHOH$—$CH_2$—$CO_2R^{13}$
—$(CH_2)_m$—$NHC(O)OR^{13}$
—$O(CH_2)_m$—$NHC(O)OR^{13}$
—$OCH_2CH_2CH_2CONHR^{13}$ —OCH$_2$CH$_2$NHCH$_2$(CHOH)$_2$CH$_2$CONHR$^{13}$
—OCH$_2$CH$_2$CONH(CH$_2$[(CHOH)$_2$CH$_2$NH$_2$)]$_2$,
—(CH$_2$)$_4$—NHCO$_2$R$^{13}$,
—(CH$_2$)$_4$—CONR$^{13}$R$^{13}$,
—(CH$_2$)$_4$—CO$_2$R$^{13}$
—OCH$_2$CH$_2$CONHSOCH$_2$CH$_2$N(CH$_3$)$_2$
—O—(CH$_2$)$_m$—C(=NH)—N(R$^{13}$)$_2$,
—(CH$_2$)$_n$—C(=NH)—N(R$^{13}$)$_2$,
—(CH$_2$)$_3$—NHCO$_2$R$^{13}$—(CH$_2$)$_3$CONHCO$_2$R$^{13}$
—O—(CH$_2$)$_m$—NH—NH—C(=NH)—N(R$^{13}$)$_2$,
—(CH$_2$)$_n$—NH—NH—C(=NH)—N(R$^{13}$)$_2$, or
—O—CH$_2$—CHOH—CH$_2$—NH—C(=NH)—N(R$^{13}$)$_2$;

There are four R$^6$ groups present on the ring in formula (A). Each R$^6$ may be each, independently, —R$^7$, —OR$^{11}$, —N(R$^7$)$_2$, —(CH$_2$)$_m$—OR$^8$,
—O—(CH$_2$)$_m$—OR$^8$, —(CH$_2$)$_n$—NR$^7$R$^{10}$, —O—(CH$_2$)$_m$—NR$^7$R$^{10}$,
—(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$,
—(CH$_2$CH$_2$O)$_m$—R$^8$, —O—(CH$_2$CH$_2$O)$_m$OR$^8$,
—(CH$_2$CH$_2$O)$_m$—CH$_2$CH$_2$NR$^7$R$^{10}$,
—O—(CH$_2$CH$_2$O)$_m$—CH$_2$CH$_2$NR$^7$R$^{10}$, —(CH$_2$)$_n$—C(=O)NR$^7$R$^{10}$,
—O—(CH$_2$)$_m$—C(=O)NR$^7$R$^{10}$, —(CH$_2$)$_n$—(Z)$_g$—R$^7$,
—O—(CH$_2$)$_m$—(Z)$_g$—R$^7$,
—(CH$_2$)$_n$—NR$^{10}$—CH$_2$(CHOR$^8$)(CHOR$^8$)$_n$—CH$_2$OR$^8$,
—O—(CH$_2$)$_m$—NR$^{10}$—CH$_2$(CHOR$^8$)(CHOR$^8$)$_n$—CH$_2$OR$^8$,
—(CH$_2$)$_n$—CO$_2$R$^7$, —O—(CH$_2$)$_m$—CO$_2$R$^7$, —OSO$_3$H, —O-glucuronide, —O-glucose, or

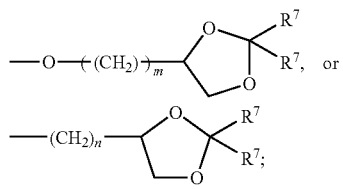

In addition, one of more of the R$^6$ groups can be one of the R$^5$ groups which fall within the broad definition of R$^6$ set forth above.

When two R$^6$ are —OR$^{11}$ and are located adjacent to each other on a phenyl ring, the alkyl moieties of the two R$^6$ groups may be bonded together to form a methylenedioxy group, i.e., a group of the formula —O—CH$_2$—O—.

As discussed above, R$^6$ may be hydrogen. Therefore, 1, 2, 3, or 4 R$^6$ groups may be other than hydrogen. Preferably at most 3 of the R$^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n maybe 0, 1, 2, 3, 4, 5, 6, or 7.

In a preferred embodiment of the invention, Y is —NH$_2$.
In another preferred embodiment, R$^2$ is hydrogen.
In another preferred embodiment, R$^1$ is hydrogen.
In another preferred embodiment, X is chlorine.
In another preferred embodiment, R$^3$ is hydrogen.
In another preferred embodiment, R$^L$ is hydrogen.
In another preferred embodiment, o is 4.
In another preferred embodiment, p is 2.
In another preferred embodiment, the sum of o and p is 6.
In another preferred embodiment, x represents a single bond.
In another preferred embodiment, R$^6$ is hydrogen.
In a preferred embodiment of the present invention:
X is halogen;
Y is —N(R$^7$)$_2$;
R$^1$ is hydrogen or C$_1$-C$_3$ alkyl;
R$^2$ is —R$^7$, —OR$^7$, CH$_2$O$^7$, or —CO$_2$R$^7$;
R$^3$ is a group represented by formula (A); and
R$^4$ is hydrogen, a group represented by formula (A), or lower alkyl;
In another preferred embodiment of the present invention:
X is chloro or bromo;
Y is —N(R$^7$)$_2$;
R$^2$ is hydrogen or C$_1$-C$_3$ alkyl;
at most three R$^6$ are other than hydrogen as described above; and
at most three R$^L$ are other than hydrogen as described above;
In another preferred embodiment of the present invention:
Y is —NH$_2$;
In another preferred embodiment of the present invention:
R$^4$ is hydrogen;
at most one R$^L$ is other than hydrogen as described above; and
at most two R$^6$ are other than hydrogen as described above.
In a preferred embodiment of the invention, Y is —NH$_2$.
In another preferred embodiment, R$^2$ is hydrogen.
In another preferred embodiment, R$^1$ is hydrogen.
In another preferred embodiment, X is chlorine.
In another preferred embodiment, R$^3$ is hydrogen.
In another preferred embodiment, R$^L$ is hydrogen.
In another preferred embodiment, o is 4.
In another preferred embodiment, p is 2.
In another preferred embodiment, the sum of o and p is 6.
In another preferred embodiment, x represents a single bond.
In another preferred embodiment, R$^6$ is hydrogen.
In a preferred embodiment of the present invention:
X is halogen;
Y is —N(R$^7$)$_2$;
R$^1$ is hydrogen or C$_1$-C$_3$ alkyl;
R$^2$ is —R$^7$, —OR$^7$, CH$_2$O$^7$, or —CO$_2$R$^7$;
R$^3$ is a group represented by formula (A); and
R$^4$ is hydrogen, a group represented by formula (A), or lower alkyl; In another preferred embodiment of the present invention:
X is chloro or bromo;
Y is —N(R$^7$)$_2$;
R$^2$ is hydrogen or C$_1$-C$_3$ alkyl;
at most three R$^6$ are other than hydrogen as described above; and
at most three R$^L$ are other than hydrogen as described above.
In another preferred embodiment of the present invention:
Y is —NH$_2$;
In another preferred embodiment of the present invention:
R$^4$ is hydrogen;
at most one R$^L$ is other than hydrogen as described above; and
at most two R$^6$ are other than hydrogen as described above.

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc.

The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA, reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. Nos. 6,264,975, 5,656,256, and 5,292,498, each of which is incorporated herein by reference.

Bronchodilators can also be used in combination with compounds of the present invention. These bronchodilators include, but are not limited to, β-adrenergic agonists including but not limited to epinephrine, isoproterenol, fenoterol, albuterol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 µm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by an suitable means know in the art, such as by nose drops, mists., etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales.

The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^4$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 (19$^{th}$ ed. 1995), incorporated herein by reference. Pharmaceutical formulations suitable for nasal administration may be prepared as described in U.S. Pat. No. 4,389,393 to Schor; U.S. Pat. No. 5,707,644 to Illum; U.S. Pat. No. 4,294,829 to Suzuki; and U.S. Pat. No. 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with as pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below:

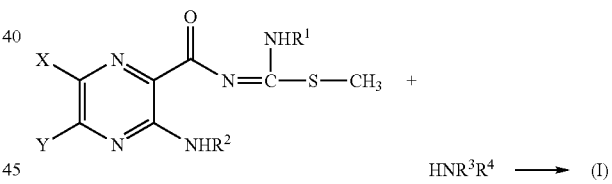

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Other methods useful for the preparation of these compounds, especially for the preparation of the novel HNR$^3$R$^4$ fragment are described in, for example, U.S. Pat. Nos. 6,858,614; 6,858,615; and 6,903,105 incorporated herein by reference. Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Using chambers. Cells obtained from freshly excised human, dog or sheep airways are seeded onto porous 0.4 micron Snapwell™ Inserts (CoStar), cultured at air-liquid interface (ALI) conditions in hormonally defined media, and assayed for sodium transport activity ($I_{SC}$ in $\mu A/cm^2$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Six preparations are typically run in parallel; one preparation per run incorporates a positive control. All data from the voltage clamps are collected via a computer interface and analyzed off-line.

Dose-effect relationships for all compounds are considered and analyzed by the Prism 3.0 program. $EC_{50}$ values, maximal effective concentrations are calculated and compared to positive controls.

In Vitro Durability of Sodium Channel Blockers: Surface Liquid Absorption, Transport, and Metabolic Profile The airway bronchial epithelium is an absorptive epithelium (actively absorbs sodium and therefore water from the lumenal to serosal direction. Using a gravimetric (weighing) procedure, the lumenal surface liquid is weighed and changes recorded up to 36 h. An applied starting volume of buffer (modified Krebs-Henseleit Bicarbonate buffer solution) with and without equimolar concentrations of selected novel or commercially available sodium channel blockers are added to the starting buffer, and at selected time points the lumenal surface liquid mass is weighed and the mass recorded in mg. In addition, during the assay, samples are collected from both the surface liquid and serosal compartment, after which the wells re-weighted and weights recorded. The samples collected are analyzed using HPLC and or mass spectrometry, and the concentration of sodium channel blocker calculated, with any conjugate or metabolite noted.

Solubility of Compounds in Water or Sodium Chloride Solution

Compound solubility was measured in water, 0.12 or 0.9% sodium chloride solution at ambient temperature for up to 10 days. Using a UV/Visable Spectrophotometer and applying Beer's Law with the calculated extinction coefficient of amiloride (18.6 mM, absorbance values at 362 nm taken from D. Mazzo 1986) the free base concentration in solution was calculated at specified time points. All samples were stored for the duration of the experiment in a single/closure system consisting of glass vials with a stopper-top closure. The vials were maintained at ambient temperature, in the dark, and in the upright position. Compound stability was measured using reverse phase high performance liquid chromatography on the final filtered pulled sample (day 10).

Confocal Microscopy Assay of Amiloride Congener Uptake

Virtually all molecules studied fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

In Vivo Assay in Sheep

Methods

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 $\mu$m. The nebulizer was connected to a dosimetry system consisting of a solenoid valve and a source of compressed air (20 psi). The output of the nebulizer was directed into a plastic T connector; one end of which was connected to the endotracheal tube, the other was connected to, a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paired t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute™ system from Elution Solution (PO Box 5147, Charlottesville, Va. 22905) charged with a 90 g silica gel cartridge (40M FSO-0110-040155, 32-63 μm) at 20 psi (N$_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: H$_2$ at 40 ml/min., Air at 400 ml/min. Carrier gas: Split Ratio 16:1, N$_2$ flow at 15 ml/min., N$_2$ velocity at 18 cm/sec. The temperature program is 70° C. for 0-3 min, 70-300° C. from 3-10 min, 300° C. from 10-15 min.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

Synthesis of 11-[N-(3,5-diamino-6-chloropyrazine-2-carbonyl)guanidino]undecanoic acid (ALB 26795)

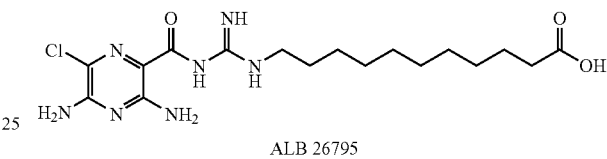

ALB 26795

11-[N-(3,5-Diamino-6-chloropyrazine-2-carbonyl) guanidino]undecanoic acid (2, ALB 26795)

Diisopropylethylamine (1.05 mL, 6.01 mmol) and 1-(3,5-diamino-6-chloropyrazine-2-carbonyl)-2-methylisothiourea hydriodide (600 mg, 1.54 mmol) were added sequentially to a suspension of amino acid 1 (300 mg, 1.49 mmol) in ethanol (10 mL). The reaction was heated to 75° C. for 6 hours after which time the reaction was cooled and the solvent removed under vacuum. Purification of the residue by column chromatography (silica gel, gradient of 100:0:0 to 89:10:1 dichloromethane/methanol/ammonium hydroxide, v/v) and subsequent precipitation from ethanol gave a yellow solid (527 mg). A 100 mg aliquot of this material was dried in a vacuum oven at 60° C. for 48 hours to provide compound 2 (96 mg, 80%) as a yellow solid: $^1$H NMR (500 MHz, DMSO-d$_6$) δ 1.24-1.34 (m, 12H), 1.46-1.51 (m, 4H), 1.73-1.79 (m, 2H), 2.16-2.20 (m, 2H), 3.13-3.16 (m, 2H), 6.71-0.84 (m; 2H); mp 181-191° C.; m/z (ESI) 414 [C$_{17}$H$_{28}$ClN$_7$O$_3$+H]$^+$.

Example 2

Synthesis of 11-[N-(3,5-diamino-6-chloropyrazine-2-carbonyl)guanidino]undecanoic acid (3-dimethylaminopropyl)amide (ALB 27160)

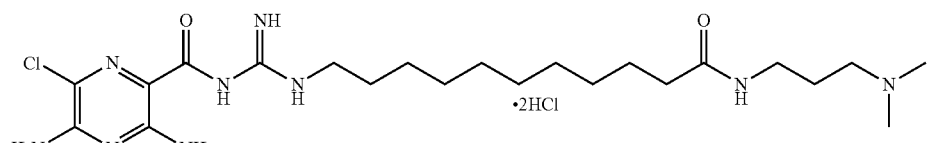

ALB 27160

11-tert-Butoxycarbonylaminoundecanoic acid (3)

Sodium hydroxide (2.18 g, 54.5 mmol) was added to a suspension of 11-aminoundecanoic acid (1) (5.00 g, 24.8 mmol) in a mixture of tetrahydrofuran and water (260 mL, 1:1). The resulting solution was stirred for 10 minutes, then di-tert-butyl dicarbonate (6.50 g, 29.8 mmol) added and the reaction stirred at ambient temperature for 14 hours. The solvent was then removed under vacuum. The resulting white solid was dissolved in chloroform, and the solution washed with a 1 N HCl (3×100 mL), dried over anhydrous magnesium sulfate and concentrated to give 3 (6.99 g, 93%) as a white solid: $^1$H NMR (500 MHz, CDCl$_3$) δ 1.28 (s, 12H), 1.44 (br, 11H), 1.56-1.66 (m, 2H), 2.34 (t, 2H, 3=7.4 Hz), 3.08-3.11 (m, 2H).

[10-(3-Dimethylaminopropylcarbamoyl)decyl]carbamic acid tert-butyl ester (4)

1,1'-Carbonyldiimidazole (118 mg, 0.73 mmol) was added to a solution of acid 3 (200 mg, 0.66 mmol) in a mixture of tetrahydrofuran (5 mL) and dichloromethane (1 mL). The resulting solution was stirred at ambient temperature for 4 h. 3-(Dimethylamino)propylamine (0.10 mL, 0.79 mmol) was then added and stirring continued for 14 hours at room temperature. The solvent was then removed under vacuum. The resulting residue was dissolved in dichloromethane (10 mL) and washed sequentially with aqueous sodium bicarbonate (1×10 mL), and then water (1×10 mL). The organic layer was dried over anhydrous sodium sulfate and concentrated to give compound 4 (154 mg, 61%) as a clear oil: $^1$H NMR (500 MHz, CDCl$_3$) δ 1.27 (m, 12H), 1.57 (br, 14H), 1.56-1.65 (m, 2H), 1.67-1.74 (m, 2H), 2.16 (t, 2H, J=7.5 Hz), 2.32 (s, 6H), 2.51 (t, 2H, J=6.7 Hz) 3.29-3.33 (m, 2H), 4.51 (br, 1H); m/z (ESI) 386 [C$_{21}$H$_{43}$N$_3$O$_3$+H]$^+$.

11-Aminoundecanoic acid (3-dimethylaminopropyl)amide dihydrochloride salt (5)

A solution of 4.0 M hydrochloric acid in dioxane (1 mL) was added dropwise to a solution of amide 4 (154 mg, 0.40 mmol) in dichloromethane (3 mL) which was pre-cooled to 0° C. After this time, the reaction was then allowed to warm to ambient temperature and stirred for an additional 2 hours. After this time, the solvent was removed under vacuum to give salt 5 (124 mg, 86%) as a white solid: $^1$H NMR (300 MHz, CD$_3$OD) δ 1.34 (s, 12H), 1.53-1.66 (m, 6H), 1.87-1.98 (m, 2H), 2.19-2.37 (m, 3H), 2.88-2.97 (m, 8H), 3.20-3.28 (m, 2H), 3.28-3.33 (m, 2H); m/z (ESI) 286 [C$_{16}$H$_{35}$N$_3$O+H]$^+$.

11-[N-(3,5-Diamino-6-chloropyrazine-2-carbonyl)guanidino]undecanoic acid (3-dimethylaminopropyl)amide (6, ALB 27160)

Diisopropylethylamine (0.30 mL, 1.72 mmol) and 1-(3,5-diamino-6-chloropyrazine-2-carbonyl)-2-methylisothiourea hydriodide (152 mg, 0.39 mmol) were added sequentially to a solution of amine 5 (122 mg, 0.34 mmol) in ethanol (5 mL). The reaction was heated to 75° C. for 6.5 hours after which time reaction was cooled and solvent removed under vacuum. Purification by column chromatography (silica gel, gradient of 100:0:0 to 89:10:1 dichloromethane/methanol/ammonium hydroxide, v/v) and then semi prep HPLC (C4 column, gradient 90:10 to 10:90 water/acetonitrile (both containing 0.05% trifluoroacetic acid)) gave the trifluoroacetic acid salt of 6 as a yellow solid. 1 M Ethereal hydrogen chloride (3×2 mL) was employed to transform the trifluoroacetic acid salt into the hydrogen chloride salt. Subsequent concentration and precipitation of the residue from methanol/diethyl ether gave compound 6 (18 mg, 9%) as a yellow solid: $^1$H NMR (500 MHz, DMSO-d$_6$) δ 1.24-1.34 (m, 14H), 1.47-1.56 (m, 4H), 1.73-1.79 (m, 2H), 2.06 (t, 2H, J=7.4 Hz), 2.71 (s, 3H), 2.72 (s, 3H), 2.96-3.01 (m, 2H), 3.06-3.11 (m, 2H), 3.26-3.30 (m, 2H), 7.42 (br, 2H), 7.96-7.98 (m, 1H), 8.73-8.97 (m, 2H), 9.20-9.22 (m, 1H), 10.33 (br, 1H), 10.50 (s, 1H); mp 52-56° C.; m/z (ESI) 498 [C$_{22}$H$_{40}$ClN$_9$O$_2$+H]$^+$.

Example 3

Synthesis of N-(3,5-diamino-6-chloropyrazine-2-carbonyl)-N-(11-oxo-11-piperazin-yl-undecyl)guanidine (ALB 27161)

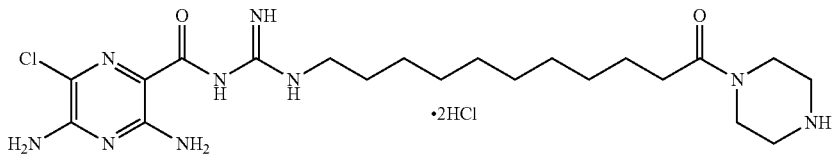

ALB 27161

4-(11-tert-Butoxycarbonylaminoundecanoyl)piperazine-1-carboxylic acid tert-butyl ester (7)

1,1'-Carbonyldiimidazole (118 mg, 0.73 mmol) was added to a solution of acid 3 (200 mg, 0.66 mmol) in tetrahydrofuran (5 mL) and the mixture stirred for 4 hours. A solution of N-tert-butoxycarbonylpiperazine (148 mg, 0.79 mmol) in tetrahydrofuran (2 mL) was added and the reaction stirred for an additional 14 hours at room temperature. The solvent was then removed under vacuum and the residual oil purified by column chromatography (silica gel, gradient 99:1 to 95:5 dichloromethane/methanol, v/v) to afford 7 (204 mg, 66%) as a white solid: $^1$H NMR (500 MHz, CDCl$_3$) δ 1.27 (m, 12H), 1.41-1.51 (m, 21H), 1.56-1.66 (m, 5H), 2.32 (t, 2H, J=7.5 Hz), 3.08-3.11 (m, 2H), 3.38-3.41 (m, 2H), 3.56-3.59 (m, 2H), 4.51 (br, 1H); m/z (ESI) 470 [C$_{25}$H$_{47}$N$_3$O$_5$+H]$^+$.

11-Amino-1-piperzin-1-yl-undecane-1-one dihydrochloride salt (8)

A solution of 4.0 M hydrochloric acid in dioxane (1 mL) was added dropwise to a solution of amide 7 (204 mg, 0.43 mmol) in dichloromethane (3 mL) which had been pre-cooled to 0° C. The reaction was allowed to warm to ambient temperature, stirred for 2 hours, and the solvent then removed under vacuum. Recrystallization from methanol and diethyl ether produced salt 8 (123 mg, 84%) as a white solid: $^1$H NMR (300 MHz, CD$_3$OD) δ 1.34 (s, 12H), 1.58-1.66 (m, 4H), 2.43 (t, 2H, J=7.4 Hz), 2.90 (t, 2H, J=7.5 Hz), 3.20-3.28 (m, 4H), 3.78-3.83 (m, 4H); m/z (ESI) 270 [C$_{15}$H$_{31}$N$_3$O+H]$^+$.

N-(3,5-Diamino-6-chloropyrazine-2-carbonyl)-N-(11-oxo-11-piperazin-yl-undecyl)-guanidine (9, ALB 27161)

Diisopropylethylamine (0.27 mL, 1.55 mmol) and 1-(3,5-diamino-6-chloropyrazine-2-carbonyl)-2-methylisothiourea hydriodide (161 mg, 0.41 mmol) were added sequentially to a solution of amine 8 (123 mg, 0.36 mmol) in ethanol (5 mL). The reaction was heated to 75° C. for 6.5 hours then cooled and the solvent removed under vacuum. Purification of the residue by column chromatography (silica gel, gradient of 100:0:0 to 89:10:1 dichloromethane/methanol/ammonium hydroxide, v/v) and then semi prep HPLC (C4 column, gradient 90:10 to 10:90 water/acetonitrile (both containing 0.05% trifluoroacetic acid)) gave the trifluoroacetic acid salt of 9 as a yellow solid. 1 M Ethereal hydrogen chloride (3×2 mL) was employed to transform the trifluoroacetic acid salt into the hydrogen chloride salt. Subsequent concentration and precipitation from methanol/diethyl ether gave compound 9 (32.0 mg, 16%) as a yellow solid: $^1$H NMR (500 MHz, DMSO-d$_6$) δ 1.26-1.31 (m, 12H), 1.47-1.55 (m, 4H), 2.31 (t, 2H, J=7.4 Hz), 3.01-3.09 (m, 4H), 3.26-3.30 (m, 2H), 7.42 (br, 2H), 8.73-8.97 (m, 2H), 9.21-9.28 (m, 3H), 10.50 (s, 1H); mp 212-215° C. dec.; m/z (ESI) 482 [C$_{21}$H$_{36}$ClN$_9$O$_2$+H]$^+$.

Example 4

Synthesis of 11-[N-(3,5-diamino-6-chloropyrazine-2-carbonyl)guanidino]undecanoic acid amide (ALB 27317)

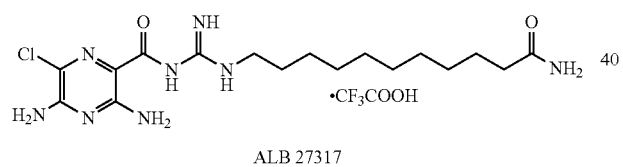

ALB 27317

(10-Carbamoyldecyl)carbamic acid tert-butyl ester (3)

1,1'-Carbonyldiimidazole (118 mg, 0.73 mmol) was added to a solution of 3 (200 mg, 0.66 mmol) in tetrahydrofuran (5 mL) and the mixture stirred at 55° C. for 3 hour. The solution was then cooled to ambient temperature and ammonia gas passed through the solution for 15 min. The reaction vessel was then sealed and the mixture stirred for 14 hours at room temperature. After this time, the solvent was removed under vacuum and the white residue purified by column chromatography (silica gel, gradient 99:1 to 90:10 dichloromethane/methanol, v/v) to afford product 10 (163 mg, 82%) as a white solid: $^1$H NMR (300 MHz, CDCl$_3$) δ 1.28 (s, 12H), 1.44 (br, 11H), 1.56-1.66 (m, 2H), 2.20-2.36 (m, 2H), 3.08-3.11 (m, 2H).

11-Aminoundecanoic acid amide trifluoroacetic acid salt (11)

Trifluoroacetic acid (4 mL) was added dropwise to a solution of amide 10 (163 mg, 0.54 mmol) in dichloromethane (4 mL) while stirring at 0° C. The reaction was then allowed to warm to ambient temperature over a 1 hour period. After this time, the solvent was removed under vacuum to afford 11 (212 mg) as a waxy solid which was contaminated with trifluoroacetic acid. This material was used directly: $^1$H NMR (300 MHz, CD$_3$OD) δ 1.33 (s, 12H), 1.58-1.66 (m, 4H), 2.20-2.28 (m, 2H), 2.90 (t, 2H, J=7.4 Hz).

11-[N-(3,5-Diamino-6-chloropyrazine-2-carbonyl) guanidino]undecanoic acid amide (12, ALB 27317)

Diisopropylethylamine (0.48 mL, 2.75 mmol) and 1-(3,5-diamino-6-chloropyrazine-2-carbonyl)-2-methylisothiourea hydriodide (250.0 mg, 0.64 mmol) were added sequentially to a solution of amine 11 (170 mg, 0.54 mmol) in ethanol (8 mL). The reaction was heated to 75° C. for 6 hours, cooled and the solvent removed under vacuum. Subsequent purification by column chromatography (silica gel, gradient of 100:0:0 to 89:10:1 dichloromethane/methanol/ammonium hydroxide, v/v) and then semi prep HPLC (C4 column, gradient 90:10 to 10:90 water/acetonitrile (both containing 0.05% trifluoroacetic acid)), gave compound 12 (25.0 mg, 11%) as an off-white solid: $^1$H NMR (300 MHz, DMSO-d$_6$) δ 1.25 (br, 12H), 1.41-1.65 (m, 4H), 2.01 (t, 2H, J=7.4 Hz), 3.21-3.30 (m, 3H), 6.69 (br, 1H), 7.21 (br, 1H), 7.40 (br, 2H), 8.73-8.97 (m, 2H), 9.11 (m, 1H), 10.46 (s, 1H); mp 69-72° C.; m/z (ESI) 413 [C$_{17}$H$_{29}$ClN$_8$SO$_2$+H]$^+$.

Example 5

Synthesis of 12-[N'-(3,5-diamino-6-chloropyrazine-2-carbonyl)guanidino]-dodecanoic acid (ALB 26799)

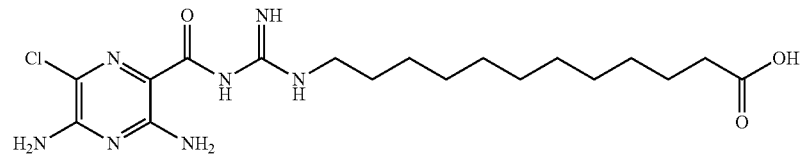

ALB 26799

A solution of 12-aminododecanoic acid (1) (0.096 g, 0.45 mmol) and diisopropylethylamine (0.39 mL, 2.23 mmol) in absolute ethanol (5 mL) was stirred at 70° C. for 30 min. 1-(3,5-Diamino-6-chloropyrazine-2-carbonyl)-2-methyl-isothiourea hydriodide (191 mg, 0.49 mmol) was added in one portion and heating at 70° C. was continued for a further 16 hours. After this time, the reaction was cooled to room and the resulting yellow precipitate collected by filtration and washed with ethanol (2×2 mL). Further purification by Biotage silica gel column chromatography using a gradient of 3% to 20% of 10% concentrated aqueous ammonium hydroxide in methanol to dichloromethane afforded acid 2 (96 mg, 50%) as a yellow solid: $^1$H NMR (500 MHz, DMSO-$d_6$) δ 1.25 (m, 14H), 1.50 (m, 4H), 2.18 (t, 2H), 3.15 (t, 2H), 6.92 (m, 3H). m/z (ESI) 428 $[C_{18}H_{30}ClN_7O_3+H]^+$. mp 194-196° C.

Example 6

Synthesis of 12-[N'-(3,5-diamino-6-chloropyrazine-2-carbonyl)guanidino]-dodecanoic acid (3-dimethylaminopropyl)amide (ALB 26982)

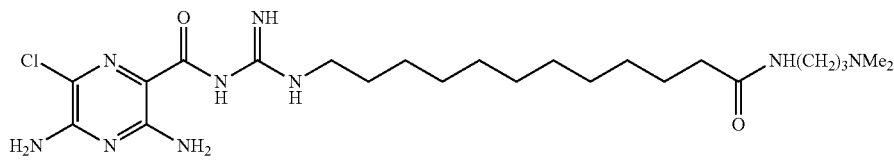

ALB 26982

[11-(3-Dimethylaminopropylcarbamoyl)undecyl]carbamic acid tert-butyl ester (4)

A mixture of 12-tert-butoxycarbonylaminododecanoic acid (3) (205 mg, 0.65 mmol) and 1,1'-Carbonyldiimidazole (114 mg, 0.70 mmol) in anhydrous THF (5 mL) was stirred at room temperature for 3 hours. 3-(Dimethylamino)propylamine (163 mL, 1.30 mmol) was then added via syringe and the reaction mixture stirred at room temperature for a further 24 hours. The solvent was then removed by rotary evaporation and the residue subjected to Biotage silica gel column chromatography (ethyl acetate/dichloromethane 5% to 75%, then methanol/dichloromethane 8%) to give the desired amide 4 (87.0 mg, 34%) as a white solid: $^1$H NMR (500 MHz, CDCl$_3$) δ 1.27 (m, 14H), 1.45 (s, 9H), 1.47 (m, 2H), 1.60 (m, 2H), 1.69 (m, 2H), 2.16 (t, 2H), 2.29 (s, 6H), 2.45 (t, 2H), 3.10 (m, 2H), 3.32 (m, 2H), 4.50 (br, 1H), 6.91 (br, 1H). m/z (ESI) 400 $[C_{22}H_{45}N_3O_3+H]^+$.

12-Aminododecanoic acid (3-dimethylaminopropyl)amide dihydrochloride (5)

[11-(3-Dimethylaminopropylcarbamoyl)undecyl]carbamic acid tert-butyl ester (4) (0.087 g, 0.22 mmol) was treated with HCl (4 M in dioxane, 2 mL, 8 mmol) and the mixture stirred at room temperature for 14 hours. The reaction was then concentrated in vacuo and further dried under high vacuum. The resulting white solid (0.081 g, 99%) was used directly without further purification. m/z (ESI) 300 $[C_{17}H_{37}N_3O+H]^+$.

12-[N'-(3,5-Diamino-6-chloropyrazine-2-carbonyl)guanidino]dodecanoic acid (3-dimethylaminopropyl)amide (6, ALB 26982)

Diisopropylethylamine (0.23 mL, 1.31 mmol) was added to a suspension of 12-amino-dodecanoic acid (3-dimethylaminopropyl)amide dihydrochloride (5) (0.081 g, 0.22 mmol) in absolute ethanol (5 mL). The mixture became homogeneous. It was stirred at 70° C. (oil bath) for 5 min and then 1-(3,5-diamino-6-chloropyrazine-2-carbonyl)-2-methylisothiourea hydriodide (0.093 g, 0.24 mmol) was added in one portion. The reaction mixture was stirred at this temperature for 3 hours and cooled to room temperature. The solvent was then removed by rotary evaporation, the residue dissolved in small volume of methanol, and this solution passed through an ion exchange resin column (Dowex 550A OH type). The resin was rinsed with methanol and the methanol solution was concentrated in vacuo. The resulting residue was purified by Biotage silica gel column chromatography, eluting with a gradient of 1% to 10% of 9:1 methanol/ammonium hydroxide in dichloromethane, to give 12-[N'-(3,5-diamino-6-chloropyrazine-2-carbonyl)guanidino]dodecanoic acid (3-dimethylaminopropyl)amide 6 (0.070 g, 63%) as a yellow solid: $^1$H NMR (300 MHz, DMSO-$d_6$) δ 1.25 (m, 14H), 1.50 (m, 6H), 2.01 (t, 2H), 2.11 (s, 6H), 2.20 (t, 2H), 3.02 (m, 2H), 3.12 (t, 2H), 6.80 (br, 3H), 7.75 (m, 1H). m/z (ESI) 512 $[C_{23}H_{42}ClN_9O_2+H]^+$. mp 82-84° C.

Example 7

Synthesis of 12-[N'-(3,5-diamino-6-chloropyrazine-2-carbonyl)guanidino]-dodecanoic acid amide (ALB 26981)

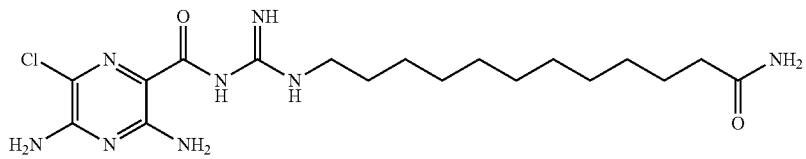

ALB 26981

(11-Carbamoylundecyl)carbamic acid tert-butyl ester (7)

A mixture of 12-tert-butoxycarbonylaminododecanoic acid (3) (202 mg, 0.64 mmol) and 1,1'-Carbonyldiimidazole (114 mg, 0.70 mmol) in anhydrous THF (6 mL) was stirred at room temperature for 1 hour. Methanolic ammonia (7 M, 3 mL, 21 mmol) was then added via syringe and the reaction mixture stirred at room temperature for 16 hours. The solvent was removed by rotary evaporation and the resulting residue was subjected to Biotage silica gel column chromatography, eluting with 5% to 36% ethyl acetate in hexanes followed by 50% ethyl acetate in dichloromethane, to give the desired amide 7 (90.0 mg, 45%) as a white solid: $^1$H NMR (500 MHz, CDCl$_3$) δ 1.25 (m, 14H), 1.46 (s, 9H), 1.63 (m, 4H), 2.22 (t, 2H), 3.10 (m, 2H), 4.50 (br, 1H), 5.40 (br, 2H). m/z (ESI) 337 [C$_{17}$H$_{34}$N$_2$O$_3$+Na]$^+$.

12-Aminododecanoic acid amide hydrochloride (8)

[(11-Carbamoylundecyl)carbamic acid tert-butyl ester (7) (0.085 g, 0.27 mmol) was treated with HCl (4 M in dioxane, 2 mL, 8 mmol) at room temperature for 14 hours. The reaction mixture was concentrated in vacuo and further dried under high vacuum. The white solid (0.068 g, 99%) was used directly without further purification: m/z (ESI) 215 [C$_{12}$H$_{26}$N$_2$O+H]$^+$.

12-[N'-(3,5-Diamino-6-chloropyrazine-2-carbonyl) guanidino]dodecanoic acid amide (9, ALB 26981)

Diisopropylethylamine (0.24 mL, 1.38 mmol) was added to a suspension of 12-amino-dodecanoic acid amide hydrochloride (8) (0.068 g, 0.27 mmol) in absolute ethanol (5 mL). The resulting solution was stirred at 70° C. (oil bath) for 5 min, after which time 1-(3,5-diamino-6-chloropyrazine-2-carbonyl)-2-methylisothiourea hydriodide (115 mg, 0.30 mmol) was added in one portion. The reaction mixture was then stirred at this temperature for 3 hours then cooled to room temperature. After removal of the solvent by rotary evaporation the resulting residue was dissolved in small volume of methanol, and the solution passed through an ion exchange resin column (Dowex 550A OH type). The resin was rinsed with methanol and the methanol solution concentrated in vacuo to a yellow residue. This residue was stirred in a minimal volume of methanol and the resulting solid was collected by suction filtration and washed with a small amount of methanol to give 12-[N'-(3,5-diamino-6-chloropyrazine-2-carbonyl)guanidino]-dodecanoic acid amide 9 (0.065 g, 56%) as a yellow solid: $^1$H NMR (300 MHz, DMSO-d$_6$) δ1.23 (m, 14H), 1.49 (m, 4H), 2.01 (t, 2H), 3.11 (m, 2H), 6.65 (m, 4H), 7.21 (br, 1H), 9.06 (br, 1H). m/z (ESI) 427 [C$_{18}$H$_{31}$ClN$_8$O$_2$+H]$^+$. mp 192-194° C.

Example 8

Synthesis of N-(3,5-diamino-6-chloropyrazine-2-carbonyl)-N'-(12-oxo-12-piperazin-1-yl-dodecyl) guanidine dihydrochloride (ALB 27069)

4-(12-tert-Butoxycarbonylaminododecanoyl)piperazine-1-carboxylic acid tert-butyl ester (10)

A mixture of 12-tert-butoxycarbonylaminododecanoic acid (3) (320 mg, 1.01 mmol) and 1,1'-carbonyldiimidazole (181 mg, 1.12 mmol) in anhydrous CH$_2$Cl$_2$ (10 mL) was stirred at room temperature for 2 hours. Then N-tert-butoxycarbonylpiperazine (227.0 mg, 1.22 mmol) was added in one portion and the reaction mixture was stirred at room temperature for 66 hours. After this time, the solvent was removed by rotary evaporation and the resulting residue was purified with Biotage silica gel column chromatography, eluting with 5% to 36% ethyl acetate/hexanes, to afford the desired amide 10 (462.0 mg, 94%) as a white solid: $^1$H NMR (500 MHz, CDCl$_3$) δ 1.25 (m, 14H), 1.42 (s, 9H), 1.47 (s, 9H), 1.62 (m, 2H), 2.30 (t, 2H), 3.10 (m, 2H), 3.42 (m, 6H), 3.60 (m, 2H), 4.49 (br, 1H). m/z (ESI) 484 [C$_{26}$H$_{49}$N$_3$O$_5$+H]$^+$.

12-Amino-1-piperazin-1-yl-dodecan-1-one dihydrochloride (11)

4-(12-tert-Butoxycarbonylaminododecanoyl)piperazine-1-carboxylic acid tert-butyl ester (10) (464 mg, 0.96 mmol) was treated with HCl (4 M in dioxane, 8 mL, 32 mmol) at room temperature for 14 hours. The reaction mixture was concentrated in vacuo and further dried under high vacuum. The white solid (342 mg, 99%) was used directly without further purification: m/z ESI 284 [C$_{16}$H$_{33}$N$_3$O+H]$^+$.

N-(3,5-Diamino-6-chloropyrazine-2-carbonyl)-N'-(12-oxo-12-piperazin-1-yl-dodecyl)guanidine dihydrochloride (12, ALB 27069)

Diisopropylethylamine (1.67 mL, 9.59 mmol) was added to a suspension of 12-amino-1-piperazin-1-yl-dodecan-1-one dihydrochloride (11) (342 mg, 0.96 mmol) in absolute ethanol (10 mL). The resulting solution was stirred at 70° C. (oil bath) for 10 min and then 1-(3,5-diamino-6-chloropyrazine-2-carbonyl)-2-methylisothiourea hydriodide (380 mg, 0.98 mmol) added in one portion. The reaction mixture was then stirred at this temperature for 3 hours and cooled to room temperature. The solvent was removed by rotary evaporation and the resulting residue was dissolved in small volume of methanol, and the solution passed through an ion exchange resin column (Dowex 550A OH type). The resin column was rinsed thoroughly with methanol and the methanol solution was concentrated in vacuo. The resulting residue was purified by Biotage silica gel column chromatography, eluting with 0% to 20% of 9:1 methanol/ammonium hydroxide in dichloromethane to give N-(3,5-diamino-6-chloropyrazine-2-carbonyl)-N-(12-oxo-12-piperazin-1-yl-dodecyl)guanidine as a yellow solid. About half of this material was further purified by preparative HPLC using acetonitrile/water/0.05% TFA. The TFA salt obtained was co-evaporated twice with aqueous 2N HCl and further dried under high vacuum to give the desired compound 12 (123 mg, 45%) as a yellow solid: $^1$H NMR (500 MHz, DMSO-d$_6$) δ 1.28 (m, 14H), 1.52 (m, 4H), 2.29 (t, 2H), 3.00 (m, 4H), 3.30 (m, 2H), 3.68 (m, 4H), 7.40 (br, 4H), 8.96 (m, 2H), 9.25 (m, 11H), 9.50 (br, 2H), 10.50 (s, 1H). m/z (ESI) 496 [C$_{22}$H$_{38}$ClN$_9$O$_2$+H]$^+$. mp 148-150° C.

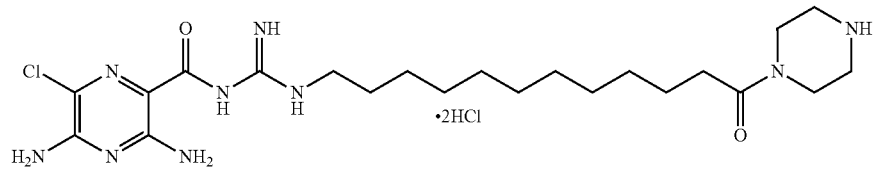

ALB 27069

Example 9

Synthesis of 12-[N'-(3,5-diamino-6-chloropyrazine-2-carbonyl)guanidino]-dodecanoic acid (1H-imidazol-2-yl)amide (ALB 27070)

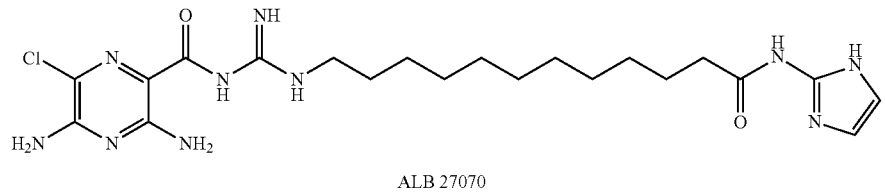

ALB 27070

[11-(1H-Imidazol-2-ylcarbamoyl)undecyl]carbamic acid tert-butyl ester (13)

DMAP (0.139 g, 1.14 mmol) and HOAt (0.062 g, 0.46 mmol) were added to a solution of 12-tert-butoxycarbonylaminododecanoic acid (3) (0.360 g, 1.14 mmol) in anhydrous DMF (5 mL). Diisopropylethylamine (1 mL, 5.71 mmol) was then added, followed by the addition of EDC.HCl (0.306 g, 1.60 mmol). The reaction mixture was stirred at room temperature for 1 hour. Then aminoimidazole hemisulfate solid (0.226 g, 1.71 mmol) was added and the reaction mixture was stirred at 50° C. (oil bath) for 66 hours. Most of the DMF solvent was removed by rotary evaporation. The residue was taken up in dichloromethane and sonicated. The insoluble solids were collected by suction filtration and subject to Biotage silica gel column chromatography, eluting with 2% methanol in dichloromethane to give the desired amide 13 (0.060 g, 14%) as an off-white solid: $^1$H NMR (500 MHz, CD$_3$OD) δ 1.30 (m, 14H), 1.40 (s, 9H), 1.68 (m, 4H), 2.40 (m, 2H), 3.00 (m, 2H), 6.78 (s, 2H). m/z (ESI) 381 [C$_{20}$H$_{36}$N$_4$O$_3$+H]$^+$.

12-Aminododecanoic acid (1H-imidazol-2-yl)amide dihydrochloride (14)

[11-(1H-Imidazol-2-ylcarbarmoyl)undecyl]carbamic acid tert-butyl ester (13) (0.060 g, 0.16 mmol) was treated with 4 M HCl in dioxane (2 mL, 8 mmol) and the mixture stirred at room temperature for 14 hours. The reaction mixture was concentrated in vacuo and further dried under high vacuum. The resulting white solid (0.056 g, 99%) was used directly without further purification. m/z (ESI) 281 [C$_{15}$H$_{28}$N$_4$O+H]$^+$.

12-[N'-(3,5-Diamino-6-chloropyrazine-2-carbonyl)guanidino]dodecanoic acid (1H-imidazol-2-yl)amide (15, ALB 27070)

Diisopropylethylamine (0.26 mL, 1.49 mmol) was added to a solution of 12-aminododecanoic acid (1H-imidazol-2-yl) amide dihydrochloride (14) (0.056 mg, 0.16 mmol) in absolute ethanol (5 mL). A white precipitate formed and the reaction was stirred at 70° C. for 10 min, then 1-(3,5-diamino-6-chloropyrazine-2-carbonyl)-2-methylisothiourea hydriodide (0.087 g, 0.22 mmol) was added in one portion. The reaction mixture was stirred at this temperature for 16 hours then cooled to room temperature. The solvent was removed by rotary evaporation and the resulting residue was dissolved in small volume of methanol and the solution passed through an ion exchange resin column (Dowex 550A OH type). The resin was rinsed with methanol and the methanol solution was concentrated in vacuo. The resulting residue was purified by Biotage silica gel column chromatography eluting with 1% to 10% of 9:1 methanol/ammonium hydroxide in dichloromethane to give 12-[N'-(3,5-diamino-6-chloropyrazine-2-carbonyl)guanidino]dodecanoic acid (1H-imidazol-2-yl) amide 15 (0.034 g, 44%) as a yellow solid: $^1$H NMR (300 MHz, DMSO-d$_6$) δ 1.25 (m, 14H), 1.50 (m, 4H), 2.29 (t, 2H), 3.09 (m, 2H), 6.61 (m, 4H). m/z (ESI) 493 [C$_{21}$H$_{33}$ClN$_{10}$O$_2$+H]$^+$. mp 102-104° C.

Example 10

Sodium Channel Blocking Activity of Selected Soluble Amides

Utilizing the tests set forth above, the data below summaries the ENaC blocking ability relative to amiloride when assayed in canine bronchial epithelium.

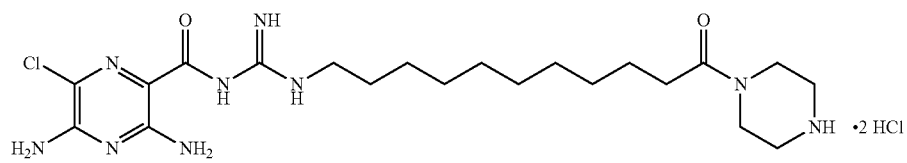

Fold Amiloride = 114

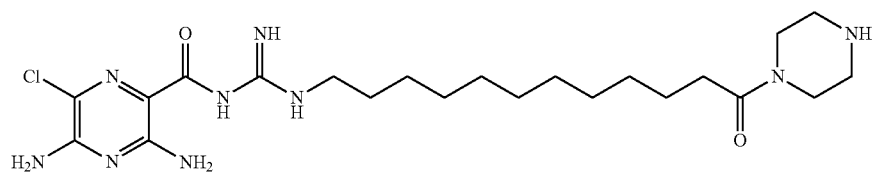

•2 HCl

Fold Amiloride = 74

-continued

Fold Amiloride = 40

Fold Amiloride = 45

Obviously, numerous modifications and variations of the present invention are possible in light of the above teachings. It is therefore to be understood that within the scope of the appended claims, the invention may be practiced otherwise than as specifically described herein.

The invention claimed is:

1. A pyrazinoylguanidine compound represented by formula (I):

(I)

wherein
X is hydrogen, halogen, or lower alkyl;
Y is hydrogen, halogen, lower alkyl, or —N(R$^2$)$_2$;
R$^1$ is hydrogen or lower alkyl;
each R$^2$ is, independently, —R$^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;
R$^3$ and R$^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of R$^3$ and R$^4$ is a group represented by formula (A):

—(C(R$^1$)$_2$)$_o$—x—(C(R$^1$)$_2$)$_p$—CR$^5$R$^6$R$^6$     (A)

wherein
each R$^1$ is, independently, —R$^7$, —(CH$_2$)—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)$_n$R$^7$R$^{10}$, —O—(CH$_2$)$_m$—C(O)$_n$R$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucose, wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;
each o is, independently, an integer from 1 to 10;
each p is an integer from 0 to 10;
with the proviso that the sum of o and p in each contiguous chain is from 1 to 10;
each x is, independently, O, NR$^{10}$, C(=O), CHOH, C(=N—R$^{10}$), CHNR$^7$R$^{10}$, or represents a single bond;
each R$^5$ is independently, —(CH$_2$)$_n$—CO$_2$R$^{13}$, Het-(CH$_2$)$_m$—CO$_2$R$^{13}$, —(CH$_2$)$_n$—Z$_g$—CO$_2$R$^{13}$, Het-(CH$_2$)$_m$—Z$_g$—CO$_2$R$^{13}$, —(CH$_2$)$_n$—NR$^{10}$—(CH$_2$)$_m$(CHOR$^8$)$_n$—CO$_2$R$^{13}$, Het-(CH$_2$)$_m$—NR$^{10}$—(CH$_2$)$_m$(CHOR$^8$)$_n$—CO$_2$R$^{13}$, —(CH$_2$)$_n$—(CHOR$^8$)$_m$—CO$_2$R$^{13}$, Het-(CH$_2$)$_m$—(CHOR$^8$)$_m$—CO$_2$R$^{13}$, —(CH$_2$)$_n$—(CHOR$^8$)$_m$Z$_g$—CO$_2$R$^{13}$, Het-(CH$_2$)$_n$—(CHOR$^8$)$_m$—Z$_g$—CO$_2$R$^{13}$, —(CH$_2$)$_n$—Z$_g$—(CH$_2$)$_m$—CO$_2$R$^{13}$, —(CH$_2$)$_n$—Z$_g$—(CH$_2$)$_m$—CO$_2$R$^{13}$, —(CH$_2$)$_n$—Z$_g$(CHOR$^8$)$_m$—Z$_g$—CO$_2$R$^{13}$, Het-(CH$_2$)$_n$—Z$_g$—(CHOR$^8$)$_m$—Z$_g$—CO$_2$R$^{13}$, —(CH$_2$)$_n$—CONH—C(=NR$^{13}$)—NR$^{13}$R$^{13}$, Het-(CH$_2$)$_n$—CO—NH—C(=NR$^{13}$)—NR$^{13}$R$^{13}$, —(CH$_2$)$_n$—Z$_g$—CONH—C(=NR$^{13}$)—NR$^{13}$R$^{13}$, Het-(CH$_2$)$_n$—Z$_g$—CONH—C(=NR$^{13}$)—NR$^{13}$R$^{13}$, —(CH$_2$)$_n$—NR$^{10}$—(CH$_{2m}$(CHOR$^8$)$_n$—CONH—C(=NR$^{13}$)—NR$^{13}$R$^{13}$, Het-(CH$_2$)$_n$—NR$^{10}$—(CH$_2$)$_m$ $(CHOR^8)_n$—CONH—C($=NR^{13}$)—$NR^{13}R^{13}$, —$(CH_2)_n$—$(CHOR^8)_m$—CONH—C($=NR^{13}$)—$NR^{13}R^{13}$, Het -$(CH_2)_n$—$(CHOR^8)_m$—CONH—C($=NR^{13}$)—$NR^{13}R^{13}$, —$(CH_2)_n$—$(CHOR^8)_m$—$Z_g$—CONH—C($=NR^{13}$)—$NR^{13}R^{13}$, Het-$(CH_2)_n$—$(CHOR^8)_m$—$Z_g$—CONH—C($=NR^{13}$)—$NR^{13}R^{13}$, —$(CH_2)_n$—$Z_g$—$(CH_2)_m$CONH—C($=NR^{13}$)—$NR^{13}R^{13}$, Het-$(CH_2)_n$—$Z_g$—$(CH_2)_m$CONH—C($=NR^{13}$)—$NR^{13}R^{13}$, —$(CH_{2n}$—$Z_g$—$(CHOR^8)_m$—$Z_g$—CONH—C($=NR^{13}$)—$NR^{13}R^{13}$, Het-$(CH_2)_n$—$Z_g$—$(CHOR^8)_m$—$Z_g$—CONH—C($=NR^{13}$)—$NR^{13}R^{13}$, —$(CH_2)_n$CONR$^7$—CONR$^{13}R^{13}$, Het-$(CH_{2n}$—CONR$^7$—CONR$^{13}R^{13}$, —$(CH_2)_n$—$Z_g$—CONR$^7$—CONR$^{13}R^{13}$, —$(CH_2)_n$—$Z_g$—CONR$^7$—CONR$^{13}R^{13}$, —$(CH_2)_n$—$NR^{10}$—$(CH_2)_m$$(CHOR^8)_n$—CONR$^7$—CONR$^{13}R^{13}$, Het-$(CH_2)_n$—$NR^{10}$—$(CH_2)_m(CHOR^8)_n$—CONR$^7$—CONR$^{13}R^{13}$, —$(CH_2)_n$—$(CHOR^8)_m$—CONR$^7$—CONR$^{13}R^{13}$, Het -$(CH_2)_n$—$(CHOR^8)_m$—CONR$^7$—CONR$^{13}R^{13}$, —$(CH_{2n}$—$(CHOR^8)_m$—$Z_g$—CONR$^7$—CONR$^{13}R^{13}$, Het-$(CH_2)_n$—$(CHOR^8)_m$—$Z_g$—CNR$^7$—CONR$^{13}R^{13}$, —$(CH_2)_n$—$Z_g$—$(CH_2)_m$CONR$^7$—CONR$^{13}R^{13}$, Het-$(CH_2)_n$—$Z_g$—$(CH_2)_m$CONR$^7$—CONR$^{13}R^{13}$, —$(CH_2)_n$—$Z_g$$(CHOR^8)_m$$Z_g$—CONR$^7$—CONR$^{13}R^{13}$, Het-$(CH_2)_n$—$Z_g$$(CHOR^8)_m$—$Z_g$—CONR$^7$—CONR$^{13}R^{13}$, —$(CH_2)_n$—CONR$^7$SO$_2$NR$^{13}R^{13}$, Het-$(CH_2)_m$—CONR$^7$SO$_2$NR$^{13}R^{13}$, —$(CH_2)_n$—$Z_g$—CONR$^7$SO$_2$NR$^{13}R^{13}$, Het-$(CH_2)_n$—$Z_g$—CONR$^7$SO$_2$NR$^{13}R^{13}$, —$(CH_2)_n$—$NR^{10}$—$(CH_2)_m$$(CHOR^8)_n$—CONR$^7$SO$_2$NR$^{13}R^{13}$, Het-$(CH_2)_m$—$NR^{10}$—$(CH_2)_m(CHOR^8)_n$—CONR$^7$SO$_2$NR$^{13}R^{13}$,—$(CH_2)_n$—$(CHOR^8)_m$—CONR$^7$SO$_2$NR$^{13}R^{13}$, Het-$(CH_2)_m$—$(CHOR^8)_m$—CONR$^7$SO$_2$NR$^{13}R^{13}$, —$(CH_2)_n$—$(CHOR^8)_m$—$Z_g$—CONR$^7$SO$_2$NR$^{13}R^{13}$, Het -$(CH_2)_n$—$(CHOR^8)_m$—$Z_g$—CONR$^7$SO$_2$NR$^{13}R^{13}$, —$(CH_2)_n$—$Z_g$—$(CH_2)_m$CONR$^7$SO$_2$NR$^{13}R^{13}$, Het-$(CH_2)_n$—$Z_g$—$(CH_2)_m$CONR$^7$SO$_2$NR$^{13}R^{13}$, —$(CH_2)_n$—$Z_g$—$(CHOR^8)_m$—$Z_g$—CONR$^7$SO$_2$NR$^{13}R^{13}$, Het-$(CH_2)_n$—$Z_g$—$(CHOR^8)_m$—$Z_g$—CONR$^7$SO$_2$NR$^{13}R^{13}$, —$(CH_2)_n$—SO$_2$NR$^{13}R^{13}$, Het-$(CH_2)_m$—SO$_2$NR$^{13}R^{13}$, —$(CH_2)_n$—$Z_g$—SO$_2$NR$^{13}R^{13}$, Het-$(CH_2)_m$—$Z_g$—SO$_2$NR$^{13}R^{13}$, —$(CH_2)_n$—NR$^{10}$—$(CH_2(_m(CHOR^8)_n$—SO$_2$NR$^{13}R^{13}$, Het-$(CH_2)_m$—NR$^{10}$—$(CH_2)_m(CHOR^8)_n$—SO$_2$NR$^{13}R^{13}$, —$(CH_2)_n$—$(CHOR^8)_m$—SO$_2$NR$^{13}R^{13}$, Het-$(CH_2)_m$—$(CHOR^8)_m$—SO$_2$NR$^{13}R^{13}$, —$(CH_2)_n(CHOR^8)_m$—$Z_g$—SO$_2$NR$^{13}R^{13}$, Het-$(CH_2)_n$—$(CHOR^8)_m$—$Z_g$—SO$_2$NR$^{13}R^{13}$, —$(CH_2)_n$—$Z_g$—$(CH_2)_m$SO$_2$NR$^{13}R^{13}$, Het-$(CH_2)_n$—$Z_g$—$(CH_2)_m$SO$_2$NR$^{13}R^{13}$, —$(CH_2)_n$—$Z_g$—$(CHOR^8)_m$—$Z_g$—SO$_2$NR$^{13}R^{13}$, Het-$(CH_2)_n$—$Z_g$—$(CHOR^8)_m$—$Z_g$—SO$_2$NR$^{13}R^{13}$, —$(CH_2)_n$—CONR$^{13}R^{13}$, Het-$(CH_2)_m$—CONR$^{13}R^{13}$, —$(CH_2)_n$—$Z_g$—CONR$^{13}R^{13}$, Het-$(CH_2)_m$—$Z_g$—CONR$^{13}R^{13}$, —$(CH_2)_n$—NR$^{10}$—$(CH_2)_m(CHOR^8)_n$—CONR$^{13}R^{13}$, Het-$(CH_2)_m$—NR$^{10}$—$(CH_2)_m(CHOR^8)_n$—CONR$^{13}R^{13}$, —$(CH_2)_n$—$(CHOR^8)_m$—CONR$^{13}R^{13}$, Het -$(CH_2)_m$—$(CHOR^8)_m$—CONR$^{13}R^{13}$, —$(CH_2)_n$—$(CHOR^8)_m$—$Z_g$—CONR$^{13}R^{13}$, Het-$(CH_2)_n$—$(CHOR^8)_m$—$Z_g$—CONR$^{13}R^{13}$, —$(CH_2)_n$—$Z_g$—$(CH_2)_m$CONR$^{13}R^{13}$, Het-$(CH_2)_n$—$Z_g$—$(CH_2)_m$CONR$^{13}R^{13}$, —$(CH_2)_n$—$Z_g$—$(CHOR^8)_m$—$Z_g$—CONR$^{13}R^{13}$, Het-$(CH_2)_n$—$Z_g$—$(CHOR^8)_m$—$Z_g$—CONR$^{13}R^{13}$, —$(CH_2)_n$—CONR$^7$COR$^{13}$, Het-$(CH_2)_m$—CONR$^7$COR$^{13}$, —$(CH_2)_n$—$Z_g$—CONR$^7$COR$^{13}$, Het -$(CH_2)_m$—$Z_g$—CONR$^7$COR$^{13}$, —$(CH_2)_n$—NR$^{10}$—$(CH_2)_m(CHOR^8)_n$—CONR$^7$COR$^{13}$, Het -$(CH_2)_m$—NR$^{10}$—$(CH_2)_m(CHOR^8)_n$—CONR$^7$COR$^{13}$, —$(CH_2)_n$—$(CHOR^8)_m$—CONR$^7$COR$^{13}$, Het-$(CH_2)_m$—$(CHOR^8)_m$—CONR$^7$COR$^{13}$, —$(CH_2)_n$—$(CHOR^8)_m$—$Z_g$—CONR$^7$COR$^{13}$, Het -$(CH_2)_n$—$(CHOR^8)_m$—$Z_g$—CONR$^7$COR$^{13}$, —$(CH_2)_n$—$Z_g$—$(CH_2)_m$CONR$^7$COR$^{13}$, —$(CH_2)_n$—$Z_g$—$(CH_2)_m$CONR$^7$COR$^{13}$, Het-$(CH_2)_n$—$Z_g$—$(CHOR^8)_m$—$Z_g$—CONR$^7$COR$^{13}$, —$(CH_2)_n$—CONR$^7$CO$_2$R$^{13}$, —$(CH_2)_n$—$Z_g$—CONR$^7$CO$_2$R$^{13}$, Het-$(CH_2)_m$—$Z_g$—CONR$^7$CO$_2$R$^{13}$, —$(CH_2)_n$—NR$^{10}$—$(CH_2)_m(CHOR^8)_n$—CONR$^7$CO$_2$R$^{13}$, Het-$(CH_2)_m$—NR$^{10}$—$(CH_2)_m(CHOR^8)_n$—CO NR$^7$CO$_2$R$^{13}$, —$(CH_2)_n$—$(CHOR^8)_m$—CONR$^7$CO$_2$R$^{13}$, Het-$(CH_2)_m$—$(CHOR^8)_m$—CONR$^7$CO$_2$R$^{13}$, —$(CH_2)_n$—$(CHOR^8)_m$—$Z_g$—CONR$^7$CO$_2$R$^{13}$, Het-$(CH_2)_n$—$(CHOR^8)_m$—$Z_g$—CONR$^7$CO$_2$R$^{13}$, —$(CH_2)_n$—$Z_g$—$(CH_2)_m$CONR$^7$CO$_2$R$^{13}$, Het-$(CH_2)_n$—$Z_g$—$(CH_2)_m$CONR$^7$CO$_2$R$^{13}$, —$(CH_2)_n$—$Z_g$—$(CHOR^8)_m$—$Z_g$—CONR$^7$CO$_2$R$^{13}$, Het-$(CH_2)_n$—$Z_g$—$(CHOR^8)_m$—$Z_g$—CONR$^7$CO$_2$R$^{13}$, —$(CH_2)_n$—NH—C($=NR^{13}$)—$NR^{13}R^{13}$, Het-$(CH_2)_m$—NH—C($=NR^{13}$)—$NR^{13}R^{13}$, —$(CH_2)_n$—$Z_g$—NH—C($=NR^{13}$)—$NR^{13}R^{13}$, Het-$(CH_2)_m$—$Z_g$—NH—C($=NR^{13}$)—$NR^{13}R^{13}$, —$(CH_2)_n$—NR$^{10}$—$(CH_2)_m(CHOR^8)_n$—NH—C($=NR^{13}$)—$NR^{13}R^{13}$, Het -$(CH_2)_m$—NR$^{10}$—$(CH_2)_m(CHOR^8)_n$—NH—C($=NR^{13}$)—$NR^{13}R^{13}$, —$(CH_2)_n$—$(CHOR^8)_m$—NH—C($=NR^{13}$)—$NR^{13}R^{13}$, Het-$(CH_2)_m$—$(CHOR^8)_m$—NH—C($=NR^{13}$)—$NR^{13}R^{13}$, —$(CH_2)_n$—$(CHOR^8)_m$—$Z_g$—NH—C($=NR^{13}$)—$NR^{13}R^{13}$, Het-$(CH_2)_n$—$(CHOR^8)_m$—$Z_g$—NH—C($=NR^{13}$)—$NR^{13}R^{13}$, —$(CH_2)_n$—$Z_g$—$(CH_2)_m$NH—C($=NR^{13}$)—$NR^{13}R^{13}$, Het-$(CH_2)_n$—$Z_g$—$(CH_2)_m$NH—C($=NR^{13}$)—$NR^{13}R^{13}$, —$(CH_2)$—$Z_g$—$(CHOR^8)_m$—$Z_g$—NH—C($=NR^{13}$)—$NR^{13}R^{13}$, Het-$(CH_2)_n$—$Z_g$—$(CHOR^8)_m$—$Z_g$—NH—C($=NR^{13}$)—$NR^{13}R^{13}$, —$(CH_2)_n$—C($=NR^{13}$)—$NR^{13}R^{13}$, Het-$(CH_2)_m$—C($=NH$)—$NR^{13}R^{13}$, —$(CH_{2n}$—$Z_g$—C($=NH$)—$NR^{13}R^{13}$, Het-$(CH_2)_m$—$Z_g$—C($=NH$)—$NR^{13}R^{13}$, —$(CH_2)_n$—NR$^{10}$—$(CH_2)_m(CHOR^8)_n$—C($=NR^{13}$)—$NR^{13}R^{13}$, Het-$(CH_2)_m$—NR$^{10}$—$(CH_2)_m(CHOR^8)_n$—C($=NR^{13}$)—$NR^{13}R^{13}$, —$(CH_2)_n$—$(CHOR^8)_m$—C($=NR^{13}$)—$NR^{13}R^{13}$, Het -$(CH_2)_m$—$(CHOR^8)_m$—C($=NR^{13}$)—$NR^{13}R^{13}$, —$(CH_2)_n$—$(CHOR^8)_m$—$Z_g$—C($=NR^{13}$)—$NR^{13}R^{13}$, Het-$(CH_2)_n$—$(CHOR^8)_m$—$Z_g$—C($=NR^{13}$)—$NR^{13}R^{13}$, —$(CH_2)_n$—$Z_g$—$(CH_2)_m$—C($=NHC(=NR^{13}$)—$NR^{13}R^{13}$, Het-$(CH_2)_n$—$Z_g$—$(CH_2)_m$—C($=N$R$^{13}$)—$NR^{13}R^{13}$, —$(CH_2)_n$—$Z_g$—$(CHOR^8)_m$—$Z_g$—C($=NR^{13}$)—$NR^{13}R^{13}$, Het-$(CH_2)_n$—$Z_g$—C($=NR^{13}$)—$NR^{13}R^{13}$;

wherein when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^6$ is, independently, —$R^5$, —$R^7$, —$OR^8$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)$$(CHOR^8)$n-$CH_2OR^8$, —O—$(CH_2)_m(CHOR^8)$$(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C($=O$)$NR^7R^{10}$, —O—

$-(CH_2)_m-C(=O)NR^7R^{10}, -(CH_2)_n-(Z)_g-R^7,$
$-O-(CH_2)_m-(Z)_g-R^7, -(CH_2)_n-NR^{10}-CH_2$
$(CHOR^8)(CHOR^8)_n-CH_2OR^8, -O-(CH_2)_m-$
$NR^{10}-CH_2(CHOR^8)(CHOR^8)_n-CH_2OR^8,$
$-(CH_2)_n-CO_2R^7, -O-(CH_2)_m-CO_2R^7,$
$-OSO_3H, -O\text{-glucose},$

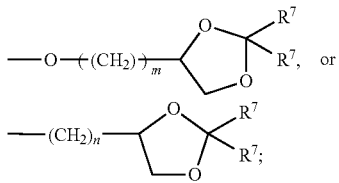

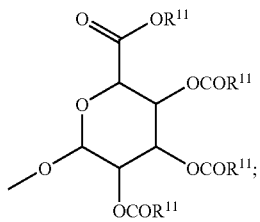

wherein when two $R^6$ are $-OR^{11}$ and are located adjacent to each other on a phenyl ring, the alkyl moieties of the two $R^6$ may be bonded together to form a methylenedioxy group, and wherein when two $-CH_2OR^8$ groups are located 1,2- or 1,3- with respect to each other the R groups may be joined to form a cyclic mono- or di-substituted 1,3-dioxane or 1,3-dioxolane;

each $R^7$ is, independently, hydrogen, lower alkyl, phenyl, substituted phenyl or $CH_2(CHOR^8)_m-R^{10}$;

each $R^8$ is, independently, hydrogen, lower alkyl, $-C(=O)-R^{11}$, 2-tetrahydropyranyl, or

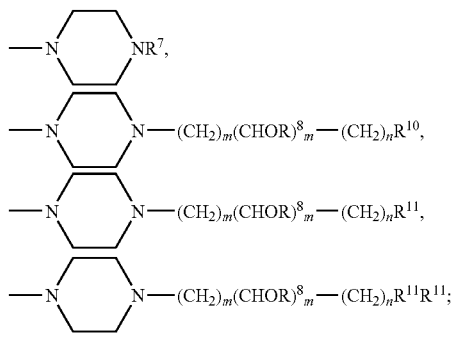

each $R^9$ is, independently, $-CO_2R^7$, $-CON(R^7)_2$, $-SO_2CH_3$, or $-C(=O)R^7$;

each $R^{10}$ is, independently, $-H$, $-SO_2CH_3$, $-CO_2R^7$, $-C(=O)NR^7R^9$, $-C(=O)R^7$, or $-(CH_2)_m-(CHOH)_n-CH_2OH$;

each Z is, independently, CHOH, $C(=O)$, $-(CH_2)_n-$, $CHNR^7R^{10}$, $C=NR^{10}$, or $NR^{10}$;

each $R^{11}$ is, independently, lower alkyl;

each $R^{12}$ is, independently, $-SO_2CH_3$, $-CO_2R^7$, $-C(=O)NR^7R^9$, $-C(=O)R^7$, or $-CH_2-(CHOH)_n-CH_2OH$;

each $R^{13}$ is, independently, hydrogen, $R^7$, $R^{10}$, $-(CH_2)_m-NR^7R^{10}$, $-(CH_2)_m-NR^7R^7$, $-(CH_2)_m-\overset{+}{NR}^{11}R^{11}R^{11}$,
$-(CH_2)_m-(CHOR^8)_m-(CH_2)_mNR^7R^{10}$, $-(CH_2)_m-NR^{10}R^{10}$
$-(CH_2)_m-(CHOR^8)_m-(CH_2)_mNR^7R^7, -(CH_2)_m-$
$(CH_2)_m\overset{+}{NR}^{11}R^{11}R^{11}, -R^7, R^{10},$

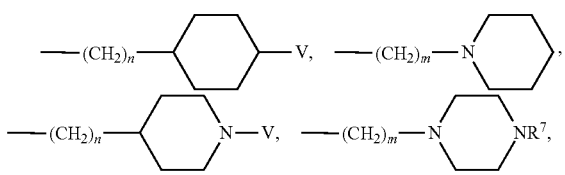

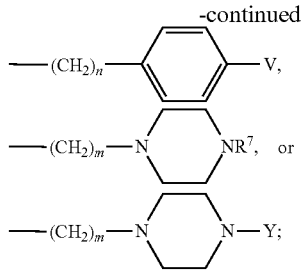

with the proviso that at least one $R^{13}$ must be a group other than hydrogen, $R^7$, or $R^{10}$;

with the further proviso that $NR^{13}R^{13}$ can be joined on itself to form a ring comprising one of the following:

each Het is independently, $-NR^7, -NR^{10}, -S-$, $-SO-, -SO_2-, -O-, -SO_2NH-, -NHSO_2-$, $-NR^7CO-$, or $-CONR^7-$;

each g is, independently, an integer from 1 to 6;
each m is, independently, an integer from 1 to 7;
each n is, independently, an integer from 0 to 7;
each V is, independently, $-(CH_2)_m-NR^7R^{10}$, $-(CH_2)_m-NR^7R^7, -(CH_2)_m-$
$\overset{+}{NR}^{11}R^{11}R^{11}, -(CH_2)_n-(CHOR^8)_m-(CH_2)_mNR^7R^{10}$, $-(CH_2)_n-NR^{10}R^{10}$
$-(CH_2)_n-(CHOR^8)_m-(CH_2)_mNR^7R^7, -(CH_2)_n-$
$(CHOR^8)_m-(CH_2)_m\overset{+}{NR}R^{11}R^{11}R^{11}$ with the proviso that when V is attached directly to a nitrogen atom, then V can also be, independently, $R^7$, $R^{10}$, or $(R^{11})_2$;

wherein for any of the above groups when two $-CH_2OR^8$ groups are located 1,2- or 1,3- with respect to each other the $R^8$ groups may be joined to form a cyclic mono- or di-substituted 1,3-dioxane or 1,3-dioxolane;

or a diastereomer and/or pharmaceutically acceptable salt thereof.

2. The compound of claim 1, wherein Y is $-NH_2$.
3. The compound of claim 2, wherein $R^2$ is hydrogen.
4. The compound of claim 3, wherein $R^1$ is hydrogen.
5. The compound of claim 4, wherein X is chlorine.
6. The compound of claim 5, wherein $R^3$ is hydrogen.
7. The compound of claim 6, wherein each $R^1$ is hydrogen.
8. The compound of claim 7, wherein o is 4.
9. The compound of claim 8, wherein p is 2.
10. The compound of claim 9, wherein x represents a single bond.
11. The compound of claim 10, wherein each $R^6$ is hydrogen.

12. The compound of claim 11, wherein $R^5$ is independently,
—$(CH_2)_n$—$CO_2R^{13}$, Het-$(CH_2)_m$—$CO_2R^{13}$, —$(CH_2)_n$—$Z_g$—$CO_2R^{13}$, Het-$(CH_2)_m$—$Z_g$—$CO_2R^{13}$, —$(CH_2)_n$—$NR^{10}$—$(CH_2)_m(CHOR^8)_n$—$CO_2R^{13}$, Het-$(CH_2)_m$—$NR^{10}$—$(CH_2)_m(CHOR^8)_n$—$CO_2R^{13}$, —$(CH_2)_n$—$(CHOR^8)_m$—$CO_2R^{13}$, Het-$(CH_2)_m$—$(CHOR^8)_m$—$CO_2R^{13}$, —$(CH_2)_n$—$(CHOR^8)_m$—$Z_g$—$CO_2R^{13}$, Het-$(CH_2)_n$—$(CHOR^8)_m$—$Z_g$—$CO_2R^{13}$, —$(CH_2)_n$—$Z_g$—$(CH_2)_m$—$CO_2R^{13}$, —$(CH_2)_n$—$Z_g$—$(CH_2)_m$—$CO_2R^{13}$, —$(CH_2)_n$—$Z_g(CHOR^8)_m$—$Z_g$—$CO_2R^{13}$, or Het-$(CH_2)_n$—$Z_g$—$(CHOR^8)_m$—$Z_g$—$CO_2R^{13}$.

13. The compound of claim 11, wherein $R^5$ is independently,
—$(CH_2)_n$—$CONH$—$C(=NR^{13})$—$NR^{13}R^{13}$, Het-$(CH_2)_n$—$CO$—$NH$—$C(=NR^{13})$—$NR^{13}R^{13}$, —$(CH_2)_n$—$Z_g$—$CONH$—$C(=NR^{13})$—$NR^{13}R^{13}$, Het-$(CH_2)_n$—$Z_g$—$CONH$—$C(=NR^{13})$—$NR^{13}R^{13}$, —$(CH_2)_n$—$NR^{10}$—$(CH_2)_m(CHOR^8)_n$—$CONH$—$C(=NR^{13})$—$NR^{13}R^{13}$, Het-$(CH_2)_n$—$NR^{10}$—$(CH_{2m}(CHOR^8)_n$—$CONH$—$C(=NR^{13})$—$NR^{13}R^{13}$, —$(CH_2)_n$—$(CHOR^8)_m$—$CONH$—$C(=NR^{13})$—$NR^{13}R^{13}$5 Het-$(CH_2)_n$—$(CHOR^8)_m$—$CONH$—$C(=NR^{13})$—$NR^{13}R^{13}$, —$(CH_2)_n$—$(CHOR^8)_m$—$Z_g$—$CONH$—$C(=NR^{13})$—$NR^{13}R^{13}$, Het-$(CH_2)_n$—$(CHOR^8)_m$—$Z_g$—$CONH$—$C(=NR^{13})$—$NR^{13}R^{13}$, —$(CH_2)_n$—$Z_g$—$(CH_2)_mCONH$—$C(=NR^{13})$—$NR^{13}R^{13}$, Het-$(CH_2)_n$—$Z_g$—$(CH_2)_mCONH$—$C(=NR^{13})$—$NR^{13}R^{13}$, —$(CH_2)_n$—$Z_g$—$(CHOR^8)_m$—$Z_g$—$CONH$—$C(=NR^{13})$—$NR^{13}R^{13}$, or Het-$(CH_2)_n$—$Z_g$—$(CHOR^8)_m$—$Z_g$—$CONH$—$C(=NR^{13})$—$NR^{13}R^{13}$.

14. The compound of claim 11, wherein $R^5$ is independently,
—$(CH_2)_n$—$CONR^7$—$CONR^{13}R^{13}$, Het-$(CH_2)_n$—$CONR^7$—$CONR^{13}R^{13}$, —$(CH_2)_n$—$Z_g$—$CONR^7$—$CONR^{13}R^{13}$, —$(CH_2)_n$—$Z_g$—$CONR^7$—$CONR^{13}R^{13}$, —$(CH_2)_n$—$NR^{10}$—$(CH_2)_m(CHOR^8)_n$—$CONR^7$—$CONR^{13}R^{13}$, Het-$(CH_2)_n$—$NR^{10}$—$(CH_2)_m(CHOR^8)_n$—$CONR^7$—$CONR^{13}R^{13}$, —$(CH_2)_n$—$(CHOR^8)_m$—$CONR^7$—$CONR^{13}R^{13}$, Het-$(CH_2)_n$—$(CHOR^8)_m$—$CONR^7$—$CONR^{13}R^{13}$, —$(CH_2)_n$—$(CHOR^8)_m$—$Z_g$—$CONR^7$—$CONR^{13}R^{13}$, Het-$(CH_2)_n$—$(CHOR^8)_m$—$Z_g$—$CNR^7$—$CONR^{13}R^{13}$, —$(CH_2)_n$—$Z_g$—$(CH_2)_mCONR^7$—$CONR^{13}R^{13}$, Het-$(CH_2)_n$—$Z_g$—$(CH_2)_mCONR^7$—$CONR^{13}R^{13}$, —$(CH_2)_n$—$Z_g(CHOR^8)_m$—$Z_g$—$CONR^7$—$CONR^{13}R^{13}$, or Het-$(CH_2)_n$—$Z_g(CHOR^8)_m$—$Z_g$—$CONR^7$—$CONR^{13}R^{13}$.

15. The compound of claim 11, wherein $R^5$ is independently, —$(CH_2)_n$—$CONR^7SO_2NR^{13}R^{13}$, Het-$(CH_2)_m$—$CONR^7SO_2NR^{13}R^{13}$, —$(CH_2)_n$—$Z_g$—$CONR^7SO_2NR^{13}R^{13}$, Het-$(CH_2)_m$—$Z_g$—$CONR^7SO_2NR^{13}R^{13}$, —$(CH_2)_n$—$NR^{10}$—$(CH_2)_m(CHOR^8)_n$—$CONR^7SO_2NR^{13}R^{13}$, Het-$(CH_2)_m$—$NR^{10}$—$(CH_2)_m(CHOR^8)_n$—$CONR^7SO_2NR^{13}R^{13}$, —$(CH_2)_n$—$(CHOR^8)_m$—$CONR^7SO_2NR^{13}R^{13}$, Het-$(CH_2)_m$—$(CHOR^8)_m$—$CONR^7SO_2NR^{13}R^{13}$, —$(CH_2)_n$—$(CHOR^8)_m$—$Z_g$—$CONR^7SO_2NR^{13}R^{13}$, Het-$(CH_2)_n$—$(CHOR^8)_m$—$Z_g$—$CONR^7SO_2NR^{13}R^{13}$, —$(CH_2)_n$—$Z_g$—$(CH_2)_mCONR^7SO_2NR^{13}R^{13}$, Het-$(CH_2)_n$—$Z_g$—$(CH_2)_mCONR^7SO_2NR^{13}R^{13}$, —$(CH_2)_n$—$Z_g$—$(CHOR^8)_m$—$Z_g$—$CONR^7SO_2NR^{13}R^{13}$, or Het-$(CH_2)_n$—$Z_g$—$(CHOR^8)_m$—$Z_g$—$CONR^7SO_2NR^{13}R^{13}$.

16. The compound of claim 11, wherein $R^5$ is independently, —$(CH_2)_n$—$SO_2NR^{13}R^{13}$, Het-$(CH_2)_m$—$SO_2NR^{13}R^{13}$, —$(CH_2)_n$—$Z_g$—$SO_2NR^{13}R^{13}$, Het-$(CH_2)_m$—$Z_g$—$SO_2NR^{13}R^{13}$, —$(CH_2)_n$—$NR^{10}$—$(CH_2)_m(CHOR^8)_n$—$SO_2NR^{13}R^{13}$, Het-$(CH_2)_m$—$NR^{10}$—$(CH_2)_m(CHOR^8)_n$—$SO_2NR^{13}R^{13}$, —$(CH_2)_n$—$(CHOR^8)_m$—$SO_2NR^{13}R^{13}$, Het-$(CH_2)_m$—$(CHOR^8)_m$—$SO_2NR^{13}R^{13}$, —$(CH_2)_n$—$(CHOR^8)_m$—$Z_g$—$SO_2NR^{13}R^{13}$, Het-$(CH_2)_n$—$(CHOR^8)_m$—$Z_g$—$SO_2NR^{13}R^{13}$, —$(CH_2)_n$—$Z_g$—$(CH_2)_mSO_2NR^{13}R^{13}$, Het-$(CH_2)_n$—$Z_g$—$(CH_2)_mSO_2NR^{13}R^{13}$, —$(CH_2)_n$—$Z_g$—$(CHOR^8)_m$—$Z_g$—$SO_2NR^{13}R^{13}$, or Het-$(CH_2)_n$—$Z_g$—$(CHOR^8)_m$—$Z_g$—$SO_2NR^{13}R^{13}$.

17. The compound of claim 11, wherein $R^5$ is independently,
—$(CH_2)_n$—$CONR^{13}R^{13}$, Het-$(CH_2)_m$—$CONR^{13}R^{13}$, —$(CH_2)_n$—$Z_g$—$CONR^{13}R^{13}$, Het-$(CH_2)_m$—$Z_g$—$CONR^{13}R^{13}$, —$(CH_2)_n$—$NR^{10}$—$(CH_2)_m(CHOR^8)_n$—$CONR^{13}R^{13}$, Het-$(CH_2)_m$—$NR^{10}$—$(CH_2)_m(CHOR^8)_n$—$CONR^{13}R^{13}$, —$(CH_2)_n$—$(CHOR^8)_m$—$CONR^{13}R^{13}$, Het-$(CH_2)_m$—$(CHOR^8)_m$—$CONR^{13}R^{13}$, —$(CH_2)_n$—$(CHOR^8)_m$—$Z_g$—$CONR^{13}R^{13}$, Het-$(CH_2)_n$—$(CHOR^8)_m$—$Z_g$—$CONR^{13}R^{13}$, —$(CH_2)_n$—$Z_g$—$(CH_2)_mCONR^{13}R^{13}$, Het-$(CH_2)_n$—$Z_g$—$(CH_2)_mCONR^{13}R^{13}$, —$(CH_2)_n$—$Z_g$—$(CHOR^8)_m$—$Z_g$—$CONR^{13}R^{13}$, or Het-$(CH_2)_n$—$Z_g$—$(CHOR^8)_m$—$Z_g$—$CONR^{13}R^{13}$.

18. The compound of claim 11, wherein $R^5$ is independently, —$(CH_2)_n$—$CONR^7COR^{13}$, Het-$(CH_2)_m$—$CONR^7COR^{13}$, —$(CH_2)_n$—$Z_g$—$CONR^7COR^{13}$, Het-$(CH_2)_m$—$Z_g$—$CONR^7COR^{13}$, —$(CH_2)_n$—$NR^{10}$—$(CH_2)_m(CHOR^8)_n$—$CONR^7COR^{13}$, Het-$(CH_2)_m$—$NR^{10}$—$(CH_2)_m(CHOR^8)_n$—$CONR^7COR^{13}$, —$(CH_2)_n$—$(CHOR^8)_m$—$CONR^7COR^{13}$, Het-$(CH_2)_m$—$(CHOR^8)_m$—$CONR^7COR^{13}$, —$(CH_2)_n$—$(CHOR^8)_m$—$Z_g$—$CONR^7COR^{13}$, Het-$(CH_2)_n$—$(CHOR^8)_m$—$Z_g$—$CONR^7COR^{13}$, —$(CH_2)_n$—$Z_g$—$(CH_2)_mCONR^7COR^{13}$, Het-$(CH_2)_n$—$Z_g$—$(CH_2)_mCONR^7COR^{13}$, or Het-$(CH_2)_n$—$Z_g$—$(CHOR^8)_m$—$Z_g$—$CONR^7COR^{13}$.

19. The compound of claim 11, wherein $R^5$ is independently, —$(CH_2)_n$—$CONR^7CO_2R^{13}$, —$(CH_2)_nZ_g$—$CONR^7CO_2R^{13}$, Het-$(CH_2)_m$—$Z_g$—$CONR^7CO_2R^{13}$, —$(CH_2)_n$—$NR^{10}$—$(CH_2)_m(CHOR^8)_n$—$CONR^7CO_2R^{13}$, Het-$(CH_2)_m$—$NR^{10}$—$(CH_2)_m(CHOR^8)_n$—$CONR^7CO_2R^{13}$, —$(CH_2)_n$—$(CHOR^8)_m$—$CONR^7CO_2R^{13}$, Het-$(CH_2)_m$—$(CHOR^8)_m$—$CONR^7CO_2R^{13}$, —$(CH_2)_n$—$(CHOR^8)_m$—$Z_g$—$CONR^7CO_2R^{13}$, Het-$(CH_2)_n$—$(CHOR^8)_m$—$Z_g$—$CONR^7CO_2R^{13}$, —$(CH_2)_n$—$Z_g$—$(CH_2)_mCONR^7CO_2R^{13}$, Het-$(CH_2)_n$—$Z_g$—$(CH_2)_mCONR^7CO_2R^{13}$, —$(CH_2)_n$—$Z_g$—$(CHOR^8)_m$—$Z_g$—$CONR^7CO_2R^{13}$, or Het-$(CH_2)_n$—$Z_g$—$(CHOR^8)_m$—$Z_g$—$CONR^7CO_2R^{13}$.

20. The compound of claim 11, wherein $R^5$ is independently,
—$(CH_2)_n$—$NH$—$C(=NR^{13})$—$NR^{13}R^{13}$, Het-$(CH_2)_m$—$NH$—$C(=NR^{13})$—$NR^{13}R^{13}$, —$(CH_2)_n$—$Z_g$—$NH$—$C(=NR^{13})$—$NR^{13}R^{13}$, Het-$(CH_2)_m$—$Z_g$—$NH$—$C(=NR^{13})$—$NR^{13}R^{13}$, —$(CH_2)_n$—$NR^{10}$—$(CH_2)_m(CHOR^8)_n$—$NH$—$C(=NR^{13})$—$NR^{13}R^{13}$, Het-$(CH_2)_m$—$NR^{10}$—$(CH_2)_m(CHOR^8)_n$—$NH$—$C(=NR)$—$NR^{13}R^{13}$, —$(CH_2)_n$—$(CHOR^8)_m$—$NH$—$C(=NR^{13})NR^{13}R^{13}$, Het-$(CH_2)_m$—$(CHOR^8)_m$—$NH$—$C(=NR^{13})$—$NR^{13}R^{13}$, —$(CH_2)_n$—$(CHOR^8)_m$—$Z_g$—$NH$—$C(=NR^{13})$—$NR^{13}R^{13}$, Het-$(CH_2)_n$—$(CHOR^8)_m$—$Z_g$—$NH$—$C(=NR^{13})$—$NR^{13}R^{13}$, —$(CH_2)_n$—$Z_g$—$(CH_2)_mNH$—$C(=NR^{13})$—$NR^{13}R^{13}$, Het-$(CH_2)_n$—$Z_g$—$(CH_2)_mNH$—$C(=NR^{13})$—$NR^{13}R^{13}$, —$(CH_2)_n$—$Z_g$—$(CHOR^8)_m$—$Z_g$—$NH$—$C(=NR^{13})$—$NR^{13}R^{13}$, Het-$(CH_2)_n$—$Z_g$—$(CHOR^8)_m$—$Z_g$—$NH$—$C(=NR^{13})$—$NR^{13}R^{13}R$, —$(CH_2)_n$—$C(=NR^{13})$—$NR^{13}R^{13}$, Het-$(CH_2)_m$—$C(=NH)$—$NR^{13}R^{13}$, —$(CH_2)_n$—$Z_g$—$C(=NH)$—$NR^{13}R^{13}$, Het-$(CH_2)_m$—$Z_g$—$C(=NH)$—$NR^{13}R^{13}$, or —$(CH_2)_n$—$NR^{10}$—$(CH_2)_m(CHOR^8)_n$—$C(=NR^{13})$—$NR^{13}R^{13}$.

21. The compound of claim 11, wherein $R^5$ is independently, $-(CH_2)_n-C(=NR^{13})-NR^{13}R^{13}$, Het-$(CH_2)_m-C(=NH)-NR^{13}R^{13}$, $-(CH_2)_n-Z_g-C(=NH)-NR^{13}R^{13}$, Het-$(CH_2)_m-Z_g-C(=NH)-NR^{13}R^{13}$, $-(CH_2)_n-NR^{10}-(CH_2)_m(CHOR^8)_n-C(=NR^{13})-NR^{13}R^{13}$, Het -$(CH_2)_m-NR^{10}-(CH_2)_m(CHOR^8)_n-C(=NR^{13})-NR^{13}R^{13}$, $-(CH_2)_n-(CHOR^8)_m-C(=NR^{13})-NR^{13}R^{13}$, Het-$(CH_2)_m-(CHOR^8)_m-C(=NR^{13})-NR^{13}R^{13}$, $-(CHOR^8)_m-Z_g-C(=NR^{13})-NR^{13}R^{13}$, Het -$(CH_2)_n-(CHOR^8)_m-Z_g-C(=NR^{13})-NR^{13}R^{13}$, $-(CH_2)_n-Z_g-(CH_2)_m-C(=NR^{13})-NR^{13}R^{13}$, Het -$(CH_2)_n-Z_g-(CH_2)_m-C(=N\ R^{13})-NR^{13}R^{13}$, $-(CH_2)_n-Z_g-(CHOR^8)_m-Z_g-C(=NR^{13})-NR^{13}R^{13}$, or Het -$(CH_2)_n-Z_g-(CHOR^8)_m-Z_g-C(-NR^{13})-NR^{13}R^{13}$.

22. The compound of claim 1, wherein $R^5$ is selected from $-(CH_2)_n-CO_2R^{13}$, Het-$(CH_2)_m-CO_2R^{13}$, $-(CH_2)_n-Z_g-CO_2R^{13}$, Het-$(CH_2)_m-Z_g-CO_2R^{13}$, $-(CH_2)_n-NR^{10}-(CH_2)_m(CHOR^8)_n-CO_2R^{13}$, Het-$(CH_2)_m-NR^{10}-(CH_2)_m(CHOR^8)_n-CO_2R^{13}$, $-(CH_2)_n-(CHOR^8)_m-CO_2R^{13}$, Het-$(CH_2)_m-(CHOR^8)_m-CO_2R^{13}$, $-(CH_2)_n-(CHOR^8)mZ_g-CO_2R^{13}$, Het-$(CH_2)_n-(CHOR^8)_m-Z_g-CO_2R^{13}$, $-(CH_2)_n-Z_g-(CH_2)_m\ CO_2R^{13}$, $-(CH_2)_n-Z_g\ (CH_2)_mCO_2R^{13}$, $-(CH_2)_n-Z_g(CHOR^8)_m-Z_g-CO_2R^{13}$, or Het-$(CH_2)_n-Z_g-(CHOR^8)_m-Z_g-CO_2R^{13}$.

23. The compound of claim 1, wherein $R^5$ is selected from $-(CH_2)_n-CONH-C(=NR^{13})-NR^{13}R^{13}$, Het-$(CH_2)_n-CONH-C(=NR^{13})-NR^{13}R^{13}$, $-(CH_2)_n-Z_g-CONH-C(=NR^{13})-NR^{13}R^{13}$, Het-$(CH_2)_n-Z_g-CONH-C(=NR^{13})-NR^{13}R^{13}$, $-(CH_2)_n-NR^{10}-(CH_2)_m(CHOR^8)_n-CONH-C(=NR^{13})-NR^{13}R^{13}$, Het-$(CH_2)_n-NR^{10}-(CH_2)_m(CHOR^8)_n-CONH-C(=NR^{13})-NR^{13}R^{13}$, $-(CH_2)_n-(CHOR^8)_m-CONH-C(=NR^{13})-NR^{13}R^{13}$, Het-$(CH_2)_n-(CHOR^8)_m-CONH-C(=NR^{13})-NR^{13}R^{13}$, $-(CH_2)_n-(CHOR^8)_m-Z_g-CONH-C(=NR^{13})-NR^{13}R^{13}$, Het-$(CH_2)_n-(CHOR^8)_m-Z_g-CONH-C(=NR^{13})-NR^{13}R^{13}$, $-(CH_2)_n-Z_g-(CH_2)mCONH-C(=NR^{13})-NR^{13}R^{13}$, Het-$(CH_2)_n-Z_g-(CH_2)_mCONH-C(=NR^{13})-NR^{13}R^{13}$, $-(CH_2)_n-Z_g-(CHOR^8)_m-Z_g-CONH-C(=NR^{13})-NR^{13}R^{13}$, or Het-$(CH_2)_n-Z_g-(CHOR^8)_m-Z_g-CONH-C(=NR^{13})-NR^{13}R^{13}$.

24. The compound of claim 1, wherein $R^5$ is selected from $-(CH_2)_n-CONR^7-CONR^{13}R^{13}$, Het-$(CH_2)_n-CONR^7-CONR^{13}R^{13}$, $-(CH_2)_n-Z_g-CONR^7-CONR^{13}R^{13}$, $-(CH_2)_n-Z_g-CONR^7-CONR^{13}R^{13}$, $-(CH_2)_n-NR^{10}-(CH_2)_m(CHOR^8)_n-CONR^7-CONR^{13}R^{13}$, Het-$(CH_2)_n-NR^{10}-(CH_2)_m(CHOR^8)_n-CONR^7-CONR^{13}R^{13}$, $-(CH_2)_n-(CHOR^8)_m-CONR^7-CONR^{13}R^{13}$, Het-$(CH_2)_n-(CHOR^8)_m-CONR^7-CONR^{13}R^{13}$, $-(CH_2)_n-(CHOR^8)_m-Z_g-CONR^7-CONR^{13}R^{13}$, Het-$(CH_2)_n-(CHOR^8)_m-Z_g-CNR^7-CONR^{13}R^{13}$, $-(CH_2)_n-Z_g-(CH_2)_mCONR^7-CONR^{13}R^{13}$, Het-$(CH_2)_n-Z_g-(CH_2)_mCONR^7-CONR^{13}R^{13}$, $-(CH_2)_n-Z_g(CHOR^8)_m-Z_g-CONR^7-CONR^{13}R^{13}$, or Het-$(CH_2)_n-Z_g(CHOR^8)_m-Z_g-CONR^7-CONR^{13}R^{13}$.

25. The compound of claim 1, wherein $R^5$ is selected from $-(CH_2)_n-CONR^7SO_2NR^{13}R^{13}$, Het-$(CH_2)_m-CONR^7SO_2NR^{13}R^{13}$, $-(CH_2)_n-Z_g-CONR^7SO_2NR^{13}R^{13}$, Het-$(CH_2)_m-Z_g-CONR^7SO_2NR^{13}R^{13}$, $-(CH_2)_n-NR^{10}-(CH_2)_m(CHOR^8)_n-CONR^7SO_2NR^{13}R^{13}$, Het-$(CH_2)_n-(CHOR^8)_m-CONR^7SO_2NR^{13}R^{13}$, Het-$(CH_2)_n-(CHOR^8)_m-Z_g-CONR^7SO_2NR^{13}R^{13}$, Het-$(CH_2)_n-(CHOR^8)_m-Z_g-CONR^7SO_2NR^{13}R^{13}$, $-(CH_2)_n-Z_g-(CH_2)_mCONR^7SO_2NR^{13}R^{13}$, Het-$(CH_2)_n-Z_g-(CH_2)mCONR^7SO_2NR^{13}R^{13}$, $-(CH_2)_n-Z_g-(CHOR^8)_m-Z_g-CONR^7SO_2NR^{13}R^{13}$, or Het-$(CH_2)_n-Z_g-(CHOR^8)_m-Z_g-CONR^7SO_2NR^{13}R^{13}$.

26. The compound of claim 1, wherein $R^5$ is selected from $-(CH_2)_n-SO_2NR^{13}R^{13}$, Het-$(CH_2)_m-SO_2NR^{13}R^{13}$, $-(CH_2)_n-Z_g-SO_2NR^{13}R^{13}$, Het-$(CH_2)_m-Z_g-SO_2NR^{13}R^{13}$, $-(CH_2)_n-NR^{10}-(CH_2)_m(CHOR^8)_n-SO_2NR^{13}R^{13}$, Het-$(CH_2)_m-NR^{10}-(CH_2)_m(CHOR^8)_n-SO_2NR^{13}R^{13}$, $-(CH_2)_n-(CHOR^8)_m-SO_2NR^{13}R^{13}$, Het-$(CH_2)_m-(CHOR^8)_m-SO_2NR^{13}R^{13}$, $-(CH_2)_n(CHOR^8)_m-Z_g-SO_2NR^{13}R^{13}$, Het-$(CH_2)_n(CHOR^8)_m-Z_g-SO_2NR^{13}R^{13}$, $-(CH_2)_n-Z_g-(CH_2)_mSO_2NR^{13}R^{13}$, Het-$(CH_2)_n-Z_g-(CH_2)_mSO_2NR^{13}R^{13}$, $-(CH_2)_n-Z_g-(CHOR^8)_m-Z_g-SO_2NR^{13}R^{13}$, Het-$(CH_2)_n-Z_g-(CHOR^8)_m-Z_g-SO_2NR^{13}R^{13}$.

27. The compound of claim 1, wherein $R^5$ is selected from $-(CH_2)_n-CONR^{13}R^{13}$, Het-$(CH_2)_m-CONR^{13}R^{13}$, $-(CH_2)_n-Z_g-CONR^{13}R^{13}$, Het-$(CH_2)_m-Z_g-CONR^{13}R^{13}$, $-(CH_2)_n-NR^{10}-(CH_2)_m(CHOR^8)_n-CONR^{13}R^{13}$, Het-$(CH_2)_m-NR^{10}-(CH_2)_m(CHOR^8)_n-CONR^{13}R^{13}$, $-(CH_2)_n-(CHOR^8)_m-CONR^{13}R^{13}$, Het-$(CH_2)_m-(CHOR^8)_m-CONR^{13}R^{13}$, $-(CH_2)_n-(CHOR^8)_m-Z_g-CONR^{13}R^{13}$, Het-$(CH_2)_n-(CHOR^8)_m-Z_g-CONR^{13}R^{13}$, $-(CH_2)_n-Z_g-(CH_2)_mCONR^{13}R^{13}$, Het-$(CH_2)_n-Z_g-(CH_2)_mCONR^{13}R^{13}$, $-(CH_2)_n-Z_g-(CHOR^8)_m-Z_g-CONR^{13}R^{13}$, or Het-$(CH_2)_n-Z_g-(CHOR^8)_m-Z_g-CONR^{13}R^{13}$.

28. The compound of claim 1, wherein $R^5$ is selected from $-(CH_2)_n-CONR^7COR^{13}$, Het-$(CH_2)_m-CONR^7COR^{13}$, $-(CH_2)_n-Z_g-CONR^7COR^{13}$, Het -$(CH_2)_m-Z_g-CONR^7COR^{13}$, $-(CH_2)_n-NR^{10}-(CH_2)_m(CHOR^8)_n-CONR^7COR^{13}$, Het-$(CH_2)_m-NR^{10}-(CH_2)_m(CHOR^8)_n-CONR^7COR^{13}$, $-(CH_2)_n-(CHOR^8)_m-CONR^7COR^{13}$, Het-$(CH_2)_m-(CHOR^8)_m-CONR^7COR^{13}$, $-(CH_2)_n-(CHOR^8)_m-Z_g-CONR^7COR^{13}$, Het-$(CH_2)_n-(CHOR^8)_m-Z_g-CONR^7COR^{13}$, $-(CH_2)_n-Z_g-(CH_2)_mCONR^7COR^{13}$, $-(CH_2)_n-Z_g-(CH_2)_mCONR^7COR^{13}$, or Het -$(CH_2)_n-Z_g-(CHOR^8)_m-Z_g-CONR^7COR^{13}$.

29. The compound of claim 1, wherein $R^5$ is selected from $-(CH_2)_n-CONR^7CO_2R^{13}$, $-(CH_2)_n-Z_g-CONR^7CO_2R^{13}$, Het-$(CH_2)_m-Z_g-CONR^7CO_2R^{13}$, $-(CH_2)_n-NR^{10}-(CH_2)_m(CHOR^8)_n-CONR^7CO_2R^{13}$, Het-$(CH_2)_m-NR^{10}-(CH_2)_m(CHOR^8)_n-CO\ NR^7CO_2R^{13}$, $-(CH_2)_n-(CHOR^8)_m-CONR^7CO_2R^{13}$, Het-$(CH_2)_m-(CHOR^8)_m-CONR^7CO_2R^{13}$, $-(CH_2)_n-(CHOR^8)_m-Z_g-CONR^7CO_2R^{13}$, Het-$(CH_2)_n-(CHOR^8)_m-Z_g-CONR^7CO_2R^{13}$, $-(CH_2)_n-Z_g-(CH_2)_mCONR^7CO_2R^{13}$, Het-$(CH_2)_n-Z_g-(CH_2)_mCONR^7CO_2R^{13}$, $-(CH_2)_n-Z_g-(CHOR^8)_m-Z_g-CONR^7CO_2R^{13}$, or Het-$(CH_2)_n-Z_g-(CHOR^8)_m-Z_g-CONR^7CO_2R^{13}$.

30. The compound of claim 1, wherein $R^5$ is selected from $-(CH_2)_n-NH-C(=NR^{13})-NR^{13}R^{13}$, Het-$(CH_2)_m-NH-C(=NR^{13})-NR^{13}R^{13}$, $-(CH_2)_n-Z_g-NH-C(=NR^{13})-NR^{13}R^{13}$, Het-$(CH_2)_m-Z_g-NH-C(=NR^{13})-NR^{13}R^{13}$, $-(CH_2)_n-NR^{10}-(CH_2)_m(CHOR^8)_n-NH-C(=NR^{13})-NR^{13}R^{13}$, Het-$(CH_2)_m-$ $NR^{10}$—$(CH_2)_m(CHOR^8)_n$—NH—C(=$NR^{13}$)—$NR^{13}R^{13}$, —$(CH_2)_n$—$(CHOR^8)_m$—NH—C(=$NR^{13}$)—$NR^{13}R^{13}$, Het-$(CH_2)_m$—$(CHOR^8)_m$—NH—C(=$NR^{13}$)—$NR^{13}R^{13}$, —$(CH_2)_n$—$(CHOR^8)_m$—$Z_g$—NH—C(=$NR^{13}$)—$NR^{13}R^{13}$, Het-$(CH_2)_n$—$(CHOR^8)_m$—$Z_g$—NH—C(=$NR^{13}$)—$NR^{13}R^{13}$, —$(CH_2)_n$—$Z_g$—$(CH_2)_m$NH—C(=$NR^{13}$)—$NR^{13}R^{13}$, Het-$(CH_2)$—$Z_g$—$(CH_2)_m$NH—C(=$NR^{13}$)—$NR^{13}R^{13}$, —$(CH_2)_n$—$Z_g$—$(CHOR^8)_m$—$Z_g$—NH—C(=$NR^{13}$)—$NR^{13}R^{13}$, Het-$(CH_2)_n$—$Z_g$—$(CHOR^8)_m$—$Z_g$—NH—C(=$NR^{13}$)—$NR^{13}R^{13}$, —$(CH_2)$—C(=$NR^{13}$)—$NR^{13}R^{13}$, Het-$(CH_2)_m$—C(=NH)—$NR^{13}R^{13}$, —$(CH_2)_n$—$Z_g$—C(=NH)—$NR^{13}R^{13}$, Het-$(CH_2)_m$—$Z_g$—C(=NH)—$NR^{13}R^{13}$, or —$(CH_2)_n$—$NR^{10}$—$(CH_2)_m$$(CHOR^8)_n$—C(=$NR^{13}$)—$NR^{13}R^{13}$.

31. The compound of claim 1, wherein $R^5$ is selected from —$(CH_2)_n$—C(=$NR^{13}$)—$NR^{13}R^{13}$, Het-$(CH_2)_m$—C(=NH)—$NR^{13}R^{13}$, —$(CH_2)_n$—$Z_g$—C(=NH)—$NR^{13}R^{13}$, Het-$(CH_2)_m$—$Z_g$—C(=NH)—$NR^{13}R^{13}$, —$(CH_2)_n$—$NR^{10}$—$(CH_2)_m$$(CHOR^8)_n$—C(=$NR^{13}$)—$NR^{13}R^{13}$, Het—$(CH_2)_m$—$NR^{10}$—$(CH_2)_m$$(CHOR^8)_n$—C(=$NR^{13}$)—$NR^{13}R^{13}$, —$(CH_2)_n$—$(CHOR^8)_m$—C(=$NR^{13}$)—$NR^{13}R^{13}$, Het-$(CH_2)_m$—$(CHOR^8)_m$—C(=$NR^{13}$)—$NR^{13}R^{13}$, —$(CH_2)_n$—$(CHOR^8)_m$—$Z_g$—C(=$NR^{13}$)—$NR^{13}R^{13}$, Het-$(CH_2)_m$—$(CHOR^8)_m$—$Z_g$—C(=$NR^{13}$)—$NR^{13}R^{13}$, —$(CH_2)_n$—$Z_g$—$(CH_2)_m$—C(=NH C(=$NR^{13}$)—$NR^{13}R^{13}$, Het-$(CH_2)_n$—$Z_g$—(CH$_2$)$_m$—C(=$NR^{13}$)—$NR^{13}R^{13}$, —$(CH_2)_n$—$Z_g$—$(CHOR^8)_m$—$Z_g$—C(=$NR^{13}$)—$NR^{13}R^{13}$, or Het-$(CH_2)_n$—$Z_g$—$(CHOR^8)_m$—$Z_g$—C(=$NR^{13}$)—$NR^{13}R^{13}$.

32. The compound of claim 1, wherein
X is chloro or bromo;
Y is —$N(R^7)_2$;
$R^1$ is hydrogen or $C_1$-$C_3$ alkyl;
$R^2$ is hydrogen or $C_1$-$C_3$ alkyl;
$R^3$ is a group represented by formula (A);
$R^4$ is hydrogen, a group represented by formula (A), or lower alkyl; at most three $R^6$ are other than hydrogen as defined above; and at most three $R^1$ are other than hydrogen as defined above.

33. The compound of claim 32, wherein
$R^4$ is hydrogen;
at most one $R^1$ is other than hydrogen as defined above; and
at most two $R^6$ are other than hydrogen as defined above.

34. The compound of claim 33, wherein
X is chloro or bromo;
Y is —$N(R^7)_2$;
$R^1$ is hydrogen or $C_1$-$C_3$ alkyl;
$R^2$ is hydrogen or $C_1$-$C_3$ alkyl;
$R^3$ is a group represented by formula (A);
$R^4$ is hydrogen, a group represented by formula (A), or lower alkyl; at most three $R^6$ are other than hydrogen as defined above; and at most three $R^1$ are other than hydrogen as defined above.

35. The compound of claim 34, wherein
$R^4$ is hydrogen;
at most one $R^1$ is other than hydrogen as defined above; and
at most two $R^6$ are other than hydrogen as defined above.

36. The compound of claim 1, wherein x is a single bond.

37. The compound of claim 1, which is in the form of a pharmaceutically acceptable salt.

38. The compound of claim 1, represented by the formula:

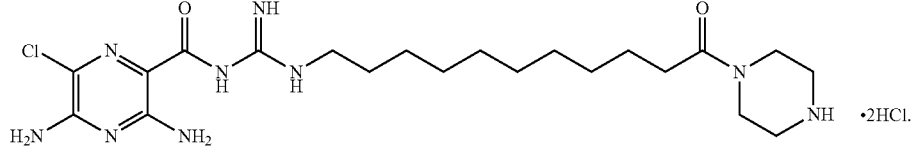

39. The compound of claim 1, represented by the formula:

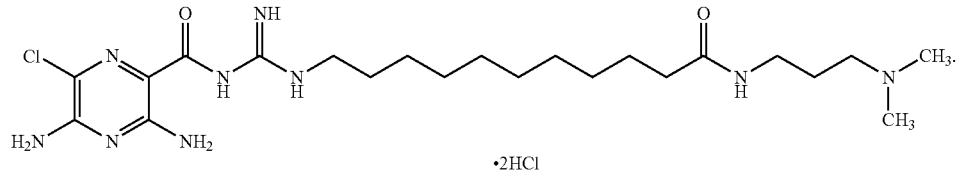

40. The compound of claim 1, represented by the formula:

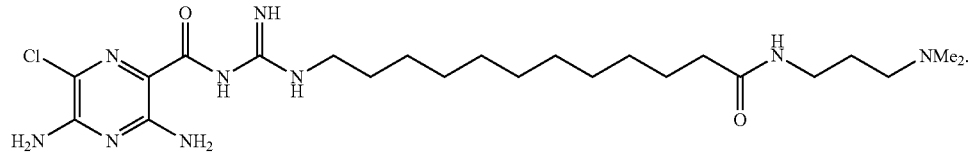

41. The compound of claim 1, represented by the formula:

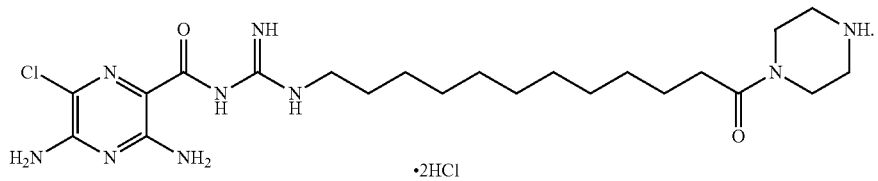

42. A pharmaceutical composition, comprising the compound of claim 1 and a pharmaceutically acceptable carrier.

43. A method of promoting hydration of mucosal surfaces, comprising:
administering an effective amount of the compound of claim 1 to a mucosal surface of a subject.

44. A method of restoring mucosal defense, comprising:
topically administering an effective amount of the compound of claim 1 to a mucosal surface of a subject in need thereof.

45. A method of promoting mucus clearance in mucosal surfaces, comprising:
administering an effective amount of the compound of claim 1 to a mucosal surface of a subject.

46. A method of promoting diuresis, comprising administering the compound of claim 1 to a subject in need thereof.

47. A method of promoting natriuresis, comprising administering the compound of claim 1 to a subject in need thereof.

48. A method of promoting saluresis, comprising administering the compound of claim 1 to a subject in need thereof.

* * * * *